US012655255B2

(12) United States Patent
Nair et al.

(10) Patent No.: US 12,655,255 B2
(45) Date of Patent: Jun. 16, 2026

(54) BIOACTIVE COMPOUND IMMOBILIZATION ON SULFONE POLYMERS

(71) Applicant: SYENSQO SPECIALTY POLYMERS USA, LLC, Alpharetta, GA (US)

(72) Inventors: Kamlesh P. Nair, Alpharetta, GA (US); Goliver DeJesus, Cumming, GA (US); Theodore Moore, Suwanee, GA (US); Emanuele Di Nicolo', Gorla Minore (IT); Keshav S. Gautam, Suwanee, GA (US)

(73) Assignee: SYENSQO SPECIALTY POLYMERS USA, LLC, Alpharetta, GA (US)

( * ) Notice: Subject to any disclaimer, the term of this patent is extended or adjusted under 35 U.S.C. 154(b) by 437 days.

(21) Appl. No.: 18/271,049

(22) PCT Filed: Feb. 9, 2022

(86) PCT No.: PCT/EP2022/053146

§ 371 (c)(1),
(2) Date: Jul. 6, 2023

(87) PCT Pub. No.: WO2022/171683

PCT Pub. Date: Aug. 18, 2022

(65) Prior Publication Data

US 2024/0026083 A1 Jan. 25, 2024

Related U.S. Application Data

(60) Provisional application No. 63/148,714, filed on Feb. 12, 2021.

(30) Foreign Application Priority Data

Jun. 9, 2021 (EP) .................................... 21178438

(51) Int. Cl.
*C08G 75/23* (2006.01)
*A61K 47/34* (2017.01)

(52) U.S. Cl.
CPC .............. *C08G 75/23* (2013.01); *A61K 47/34* (2013.01)

(58) Field of Classification Search
USPC .......................................................... 528/376
See application file for complete search history.

(56) References Cited

U.S. PATENT DOCUMENTS

| | | | |
|---|---|---|---|
| 3,766,104 A | 10/1973 | Bonin et al. |
| 5,145,583 A | 9/1992 | Angleraud et al. |
| 6,177,013 B1 | 1/2001 | Thomas et al. |
| 2013/0101546 A1 | 4/2013 | Yurkovetskiy et al. |
| 2019/0054429 A1 | 2/2019 | Di Nicolo' et al. |
| 2019/0300653 A1 | 10/2019 | Green et al. |

FOREIGN PATENT DOCUMENTS

| | | |
|---|---|---|
| EP | 0781795 A2 | 7/1997 |
| EP | 2963076 A1 | 1/2016 |
| EP | 2966109 A1 | 1/2016 |
| EP | 3822302 A1 | 5/2021 |
| WO | WO 2019048652 A1 | 3/2019 |
| WO | WO 2020187684 A1 | 9/2020 |
| WO | WO 2021048229 A1 | 3/2021 |

OTHER PUBLICATIONS

Wendel H. P. et al., "Coating-techniques to improve the hemocompatibility of artificial devices used for extracorporeal circulation", European Journal of Cardio-thoracic Surgery, 1999, 16, p. 342-350, Elsevier Science B.V.
Murugesan S. et al., "Immobilization of Heparin: Approaches and Applications", Curr Top Med Chem., 2008, 8(2), p. 80-100, Bentham Science Publishers Ltd.
Huang X.-J., "Blood Compatibility and Permeability of Heparin-Modified Polysulfone as Potential Membrane for Simultaneous Hemodialysis and LDL Removal", Macromol. Biosci., 2011, 11, p. 131-140, Wiley-VCH Verlag GmbH & Co. KGaA, Weinheim.
Biran, R. et al., "Heparin coatings for improving blood compatibility of medical devices", Advanced Drug Delivery Reviews, 2017, 112, p. 12-23, Elsevier Inc.
U.S. Appl. No. 17/437,457, Nair, Kamlesh, Thomas, David B., filed Mar. 12, 2020, US 2022-0162380 A1, WO 2020187684.

*Primary Examiner* — Terressa Boykin
(74) *Attorney, Agent, or Firm* — Beatrice C. Ortego

(57) ABSTRACT

The invention relates to a poly(aryl ether sulfone) (PAES) copolymer (P2) with ionically and/or covalently attached bioactive compound(s), articles comprising (P2), methods of making (P2), and methods for making articles such as membranes comprising (P2). Functionalized side-chain PAES copolymers (P1) permit the immobilization of a bioactive compound on copolymer's functionalized side chains for preparing bioactive articles. In particular, an antithrombotic agent such as heparin may be immobilized to form a bioactive membrane structure suitable for hemodialysis to avoid or eliminate the injection of such antithrombotic agent to a patient undergoing hemodialysis. Preferred embodiments include heparinized PAES copolymers and membranes comprising them.

18 Claims, 5 Drawing Sheets

BIOACTIVE COMPOUND IMMOBILIZATION ON SULFONE POLYMERS

CROSS-REFERENCE TO RELATED APPLICATIONS

This application is a U.S. national stage entry under 35 U.S.C. § 371 of International Application No. PCT/EP2022/053146 filed Feb. 9, 2022, which claims priority to U.S. provisional application No. 63/148,714 filed on Feb. 12, 2021 and to European patent application No. 21178438.4 filed on Jun. 9, 2021, the whole content of these applications being incorporated herein by reference for all purposes.

STATEMENT REGARDING FEDERALLY SPONSORED RESEARCH OR DEVELOPMENT

Not applicable.

TECHNICAL FIELD

The invention relates to modified PAES copolymers with an ionically and/or covalently attached bioactive compound, particularly heparinized PAES copolymers, their use in making articles and method for making articles, polymer solutions, and methods of making such modified PAES copolymers from functionalized side-chain PAES copolymers. Bioactive articles or structures may be made with such modified PAES copolymers.

BACKGROUND

Poly(aryl ether sulfone) (PAES) polymers are a class of thermoplastic polymers characterized by high glass-transition temperatures, good mechanical strength and stiffness, and outstanding thermal and oxidative resistance. By virtue of their mechanical, thermal, and other desirable characteristics, these polymers are used increasingly making products for a wide and diversified range of commercial applications, for instance in coatings, in membranes for wide field of use including medical market, due to their excellent mechanical and thermal properties, coupled with outstanding hydrolytic stability. PAES is a generic term used to describe any polymer containing at least one sulfone group (—$SO_2$—), at least one ether group (—O—) and at least one arylene group.

A commercially important group of PAES includes polysulfone polymers identified herein as polysulfones, in short PSU. PSU polymers contain recurring units derived from the condensation of the dihydroxy monomer bisphenol A (BPA) and a dihalogen monomer, for example 4,4'-dichlorodiphenyl sulfone (DCDPS). Such PSU polymers are commercially available from Solvay Specialty Polymers USA LLC under the trademark UDEL®. The structure of the recurring units of such a PSU polymer is shown below:

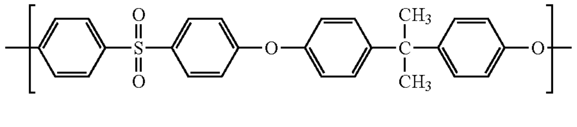

PSU polymers have a high glass transition temperature (e.g., about 185° C.) and exhibit high strength and toughness.

Another important group of PAES includes polyethersulfone polymers, in short PES. PES polymers derive from the condensation of the dihydroxy monomer bisphenol S (BPS) and a dihalogen monomer, for example 4,4'-dichlorodiphenyl sulfone (DCDPS). Such PES polymers are commercially available from Solvay Specialty Polymers USA LLC under the trademark VERADEL®. The structure of the recurring units of such a PES polymer is shown below:

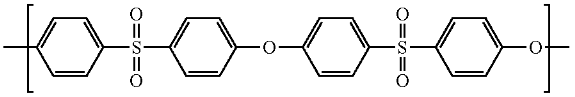

PSU and PES polymers, respectively based on BPA and BPS, are frequently used to prepare membranes to be used in contact with biological fluids, for example blood.

A wide range of medical devices, artificial organs, blood purification equipment such as hemodialysis, hemodiafiltration, hemofiltration, plasmapheresis and plasma collectors are generally equipped with PES membranes. Out of the synthetic polymers used in dialyzer membranes, 93% are derived from the polyarylsulfone family, with 22% produced from PES and 71% from PSU. Membranes in new super high-flux dialyzers include primarily PSU and PES.

When PES-based hemodialysis membranes are contacted with blood, proteins tend to adsorb onto the polymer surface, and this protein layer causes any adverse effects such as the coagulation of blood cells and platelet adhesion. Plasma proteins such as albumins, globulins, and fibrinogen in blood play key roles in coagulation and invoke the immune system against PES surface. The coagulation process may be intrinsically initiated when blood contacts with such foreign surface. The coagulation cascade starts with a thrombus reaction when blood comes into contact with the hemodialysis membrane, where fibrin clots are formed, and the resulting clots tend to adhere to the membrane surface and disrupt the blood circulation. Therefore, blood coagulation processes have limited the use of PES membrane for hemodialysis.

To address this issue of blood coagulation during hemodialysis on PAES polymer membranes, PAES can be modified using: (1) bulk modification; (2) surface modification; and (3) blending (sometimes also considered as a bulk modification). Bulk modification methods are applied to a dope solution, which modifies the entire membrane. Sulfonation and carboxylation methods were mostly reported for bulk modification.

Heparin is a naturally occurring polysaccharide that inhibits coagulation, the process that leads to thrombosis. Because heparin interrupts the coagulation and clotting of blood, it is generally administered during hemodialysis to prevent blood coagulation, even with "biocompatible" PSU or PES hemodialysis membranes. As a medication heparin is generally given by injection into a vein. Eliminating the need for heparin administration could reduce the cost for dialysis as well as improve patient outcomes. Indeed, there are side effects from heparin and some patients receiving hemodialysis are or can become allergic to heparin. In order to avoid heparin administration however, (i) there should be no clotting in blood exposed to the membrane surface and (ii) no platelets should be present on the membrane surface.

WO 2020/187684A1 (SOLVAY SPECIALTY POLYMERS USA), incorporated herein in the present description, discloses functionalized side-chain PAES copolymers, particularly with amine functionalized side chains.

Such functionalized side-chain PAES copolymers offer the possibility to attach or immobilize bioactive compounds (e.g., having anti-coagulant properties) for preparing functional membrane structures suitable for hemodialysis while avoiding or eliminating the injection of such bioactive compound(s) into the blood of the patient undergoing hemodialysis.

Therefore the present invention aims to address the above referenced issues by reducing or eliminating the need to use anti-coagulants during hemodialysis using a modified PAES based membrane.

SUMMARY

A first aspect of the present invention is directed to a bioactive compound-bound poly(aryl ether sulfones) (PAES), hereinafter "copolymer (P2)". The copolymer (P2) comprises:

recurring units ($R_{P2}$) of formula (M);

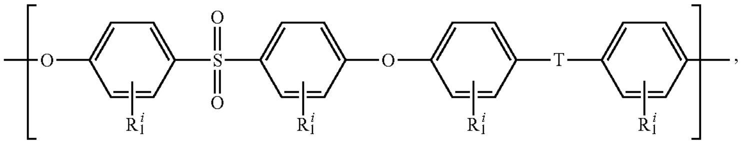

(M)

recurring units ($R^*_{P2}$) of formula (Q):

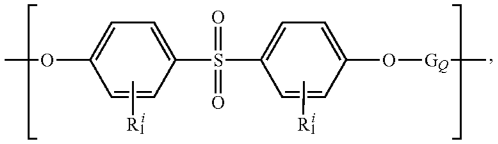

(Q)

wherein each $R_1$ is independently selected from the group consisting of a halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;

each i is an integer independently selected from 0 to 4;

T is selected from the group consisting of a bond, $-CH_2-$; $-O-$; $-SO_2-$; $-S-$; $-C(O)-$; $-C(CH_3)_2-$; $-C(CF_3)_2-$; $-C(=CCl_2)-$; $-N=N-$; $-C(CH_3)(CH_2CH_2COOH)-$; $-R_aC=CR_b-$, where each $R_a$ and $R_b$, independently of one another, is a hydrogen or a C1-C12-alkyl, C1-C12-alkoxy, or C6-C18-aryl group; $-(CF_2)_m-$ with m being an integer from 1 to 6; an aliphatic divalent group, linear or branched, of up to 6 carbon atoms, preferably-$(CH_2)_{m'}-$ with m' being an integer from 1 to 6; and combinations thereof;

$G_Q$ is at least one formula selected from formulae ($G_{Q1}$), ($G_{Q2}$), ($G_{Q3}$), ($G_{Q4}$), ($G_{Q5}$), or ($G_{Q6}$):

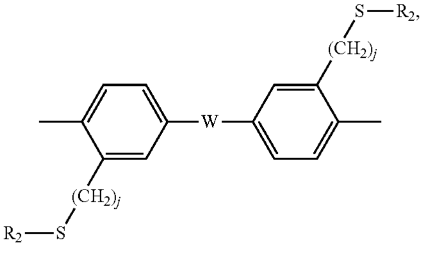

($G_{Q1}$)

-continued

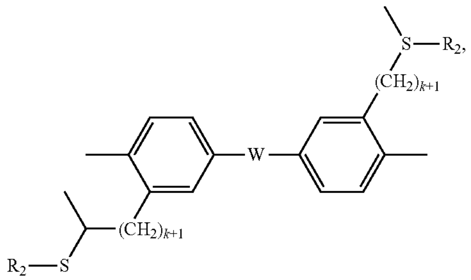

($G_{Q2}$)

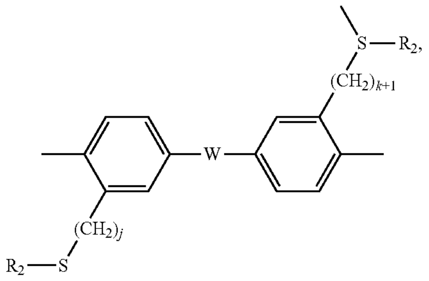

($G_{Q3}$)

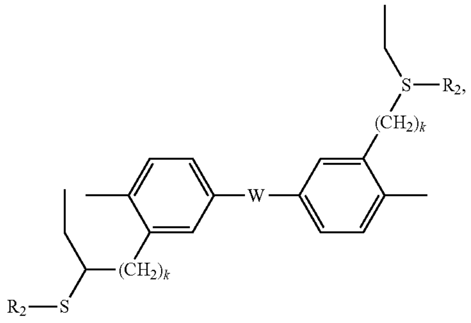

($G_{Q4}$)

-continued ($G_{Q5}$)

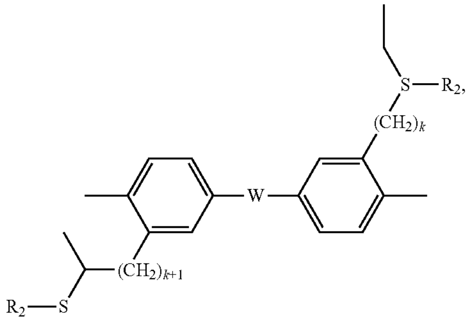

($G_{Q6}$)

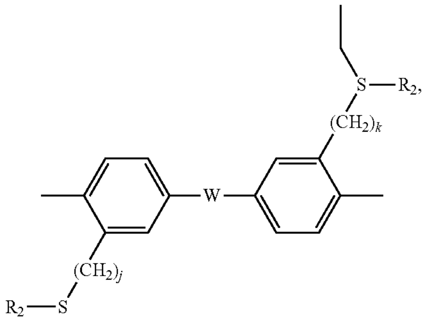

wherein each k is an integer independently selected from 0 to 4;

each j is an integer independently selected from 2 to 7;

W is a bond, $—C(CH_3)_2—$ or $—SO_2—$, preferably $—C(CH_3)_2—$ or $—SO_2—$, more preferably $—C(CH_3)_2—$;

$R_2$ is represented by the following formula: $—(CH_2)_p—NR_cB$, with p being selected from 1 to 5, with $R_c$ being independently a C1-C6 alkyl or H, and with B representing a bioactive compound (or derivative thereof) which is covalenty and/or ionically bound to $R_2$, particularly bound to the nitrogen atom in $R_2$.

Non-limiting examples of bioactive compounds or derivatives thereof “B” suitable for the present invention include:

antithrombotic agents or derivatives thereof, amino acids, nucleic acids, glucuronic acid residues, hyaluronic acid or derivatives thereof, proteins, like collagen, keratin, enzymes, metal-chelating and/or protease inhibitor agents such as EGTA and EDTA;

acidic lipids such as prostaglandins, and any combinations of two or more compounds thereof.

Preferred bioactive compounds or derivatives thereof “B” are selected from the group consisting of antithrombotic agents or derivatives thereof, such as heparin or salts thereof.

A second aspect of the present invention pertains to a process for making the copolymer (P2), comprising: contacting a copolymer (P1) with a bioactive compound or derivative thereof, optionally in the presence of a coupling agent, in an acidic aqueous solvent, preferably of pH from 3 to 6, or from 4.2 to 5, or from 4.4 to 4.8, to bind the bioactive compound to the copolymer (P1) to make the copolymer (P2).

The copolymer (P1) comprises:

recurring units ($R_{P1}$) of the formula (M) as described herein, and recurring units ($R^*_{P1}$) of formula (N):

(N)

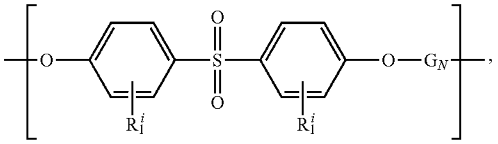

wherein each $R_1$, i and T are defined in the same manner as for the formula (M);

$G_N$ is selected from the group consisting of at least one of the following formulae ($G_{N1}$), ($G_{N2}$), ($G_{N3}$), ($G_{N4}$), ($G_{N5}$) and ($G_{N6}$):

($G_{N1}$)

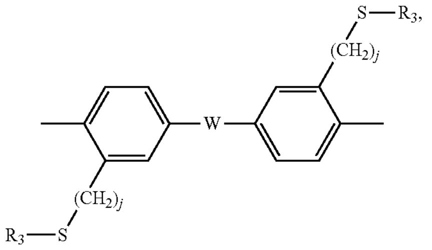

($G_{N2}$)

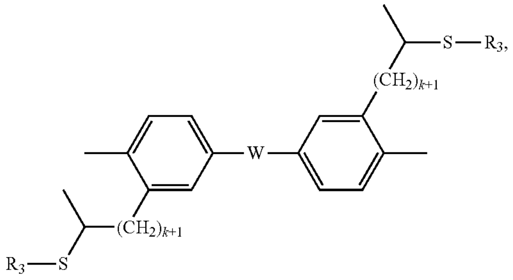

($G_{N3}$)

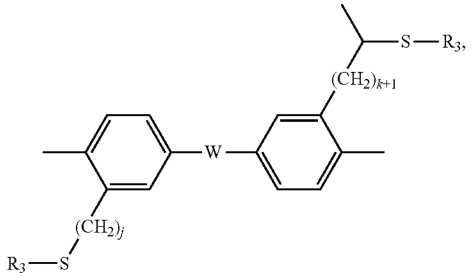

-continued ($G_{N4}$)

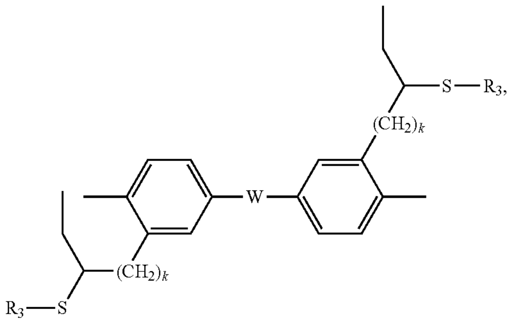

($G_{N5}$)

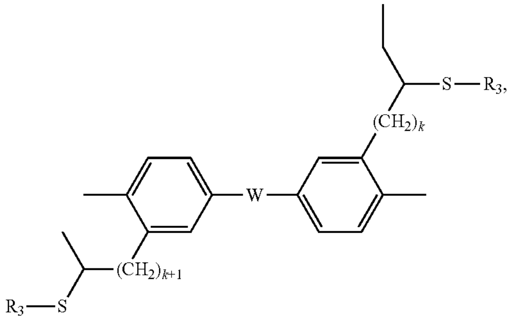

($G_{N6}$)

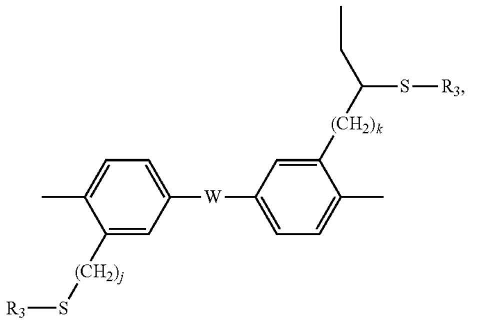

wherein each k is an integer independently selected from 0 to 4;

each j is an integer independently selected from 2 to 7;

W is a bond, $—C(CH_3)_2—$ or $—SO_2—$, preferably $—C(CH_3)_2—$ or $—SO_2—$, more preferably $—C(CH_3)_2—$;

$R_3$ is represented by the following formula: $—(CH_2)_p—NHR_c$, with p being selected from 1 to 5, with $R_c$ being independently a C1-C6 alkyl or H, preferably represented by the following formula: $—(CH_2)_p—NH_2$, more preferably represented by the following formula: $—(CH_2)_2—NH_2$.

A third aspect of the present invention relates to the use of the copolymer (P2) for the manufacture of articles such as medical devices, implants, membranes, coatings, films, fibers, sheets, and three-dimensional injected or molded or printed parts.

A fourth aspect of the present invention relates to an article comprising the copolymer (P2) described herein or the copolymer (P2) manufactured by the process described herein according to the second aspect. The article may be selected from the group consisting of medical devices, implants, membranes, coatings, melt processed films, solution processed films, melt process monofilaments and fibers, solution processed monofilaments, hollow fibers and solid fibers, coatings, printed objects, and injection and compression molded objects. The article may be a membrane or part thereof, such membrane being selected from membranes for bioprocessing and medical filtrations (such as hemodialysis membranes), membranes for food and beverage processing, membranes for water purification, membranes for waste water treatment and membranes for industrial process separations involving aqueous media. The article may be a medical device or implant.

A fifth aspect of the present invention relates to a method of making an article comprising the copolymer (P2) described herein or the copolymer (P2) manufactured by the process described according to the second aspect. The method for making an article comprising the copolymer (P2) may comprise performing one of the following:

method a): using the copolymer (P2) in forming the article or part thereof; or method b): contacting the copolymer (P1) with a bioactive compound or derivative thereof to make the copolymer (P2) while at the same time forming the article or part thereof; or method c): contacting a pre-formed article or part thereof comprising the copolymer (P1) with the bioactive compound or derivative thereof to make the copolymer (P2), wherein the polymer (P1) comprises the recurring units ($R_{P1}$) of the formula (M), and the recurring units ($R^*_{P1}$) of the formula (N), as described herein.

The contacting step may be carried out, optionally in the presence of a coupling agent, in an acidic aqueous solvent, preferably of pH from 3 to 6, or from 4.2 to 5, or from 4.4 to 4.8, to bind the bioactive compound to the copolymer (P1) to make the copolymer (P2).

The various aspects, advantages, and features of the invention will be more readily understood and appreciated by reference to the detailed description and examples.

DEFINITIONS

Figure 1:
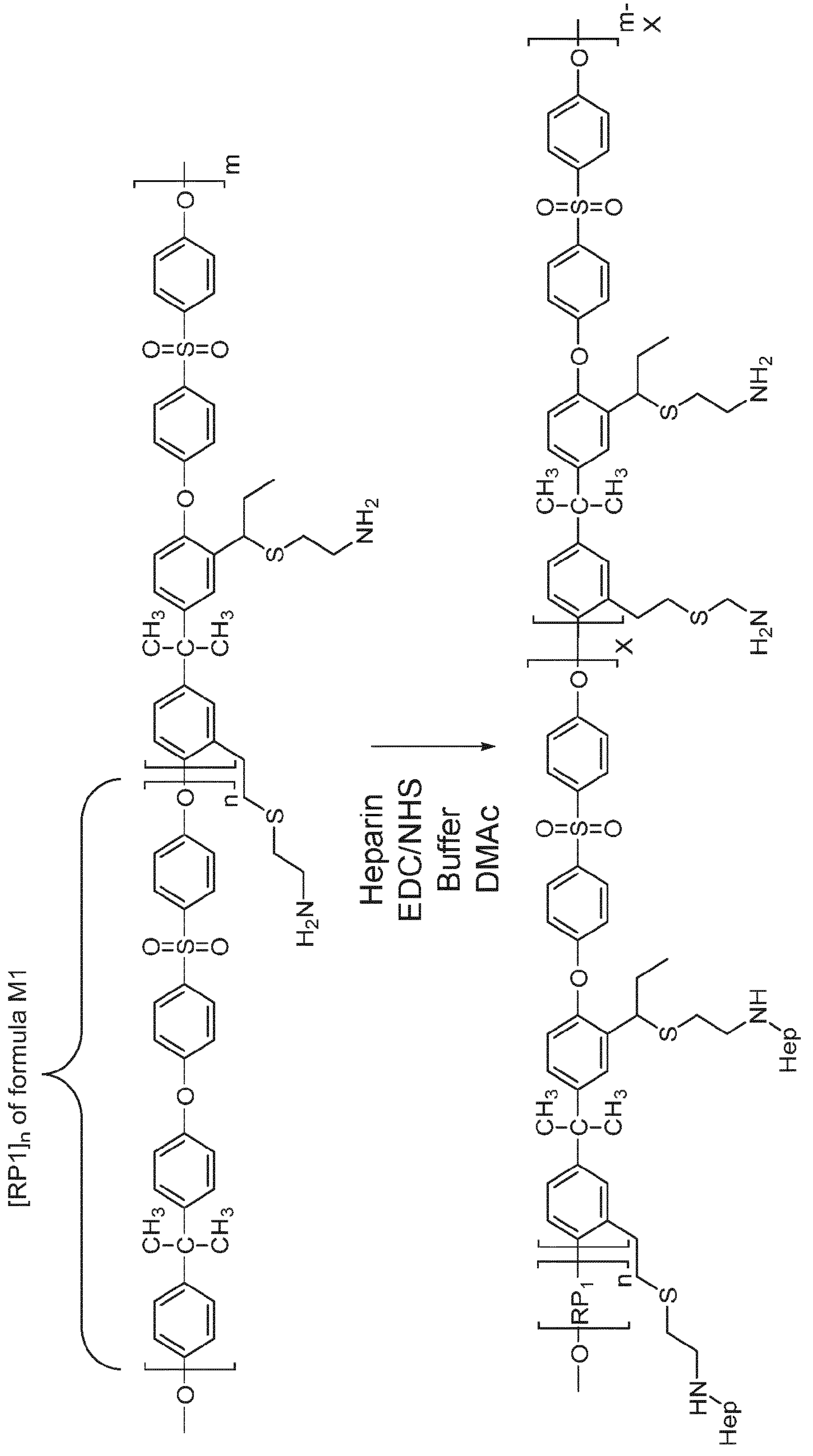
FIG. 1 illustrates a reaction scheme for making a heparin-immobilized PSU copolymer (P2) according to one embodiment.

In the present descriptive specification, some terms are intended to have the following meanings.

As used herein, the term “bioactive” in relation to a compound or structure is intended to mean that such compound or structure has a biological activity. A “bioactive” compound may present a therapeutic potential; may elicit pharmacological effects; may modulate metabolic processes; may have beneficial physiological, behavioral, or immunological effects; may have anti-oxidant, anti-carcinogenic, anti-inflammatory, anti-thrombotic or anti-microbial properties; may elicit inhibition of receptor activities; may elicit inhibition or induction of enzymes such as protease inhibitor; may elicit induction and inhibition of gene expression; may have metal-chelating properties; may act as an adsorbent to remove specific compound(s) from a fluid; or may have a catalytic activity in the body. As an example, a bioactive carbonyl compound, which bears a carbonyl group, may be involved in reactions during food production processes, owing to their functional carbonyl group. As another example, heparin-modified membrane as a bioactive structure can prevent coagulation in the blood and/or on the surface of the membrane and/or may be useful in removing low-density lipoprotein (LDL cholesterol) from blood.

As used herein, heparin is a highly sulfated glycosaminoglycan and consists of variably sulfated repeating disaccharide units. This polysaccharide typically has a MW of 3-30 kDa with an average of about 12-15 kDa, although a fractionated version of heparin also exists in a low-MW form (e.g., MW of about 3-7 kDa) such as dalteparin, enoxaparin. Without wishing to be bound by such theory, heparin is said to exert its anticoagulant activity by activating antithrombin. A derivative of heparin is preferably a salt form, such as sodium salt of heparin.

The term “solvent” is used herein in its usual meaning that, it indicates a substance capable of dissolving another substance (solute) to form a uniformly dispersed mixture at the molecular level. In the case of a polymeric solute it is common practice to refer to a solution of the polymer in a solvent when the resulting mixture is transparent and no phase separation is visible in the system. Phase separation is taken to be the point, often referred to as “cloud point”, at which the solution becomes turbid or cloudy due to the formation of polymer aggregates.

As used herein, “BPA” means Bisphenol A or 4,4'-isopropylidenediphenol; “BPS” means Bisphenol S or 4,4' dihydroxydiphenyl sulfone; “DCDPS” means 4,4'-dichlorodiphenyl sulfone; “DFDPS” means 4,4' difluorodiphenyl sulfone; EDC means N-(3-Dimethylaminopropyl)-N'-ethylcarbodiimide hydrochloride; and NHS means N-Hydroxy succinimide.

The term “membrane” is used herein in its usual meaning, that is to say it refers to a discrete, generally thin, interface that moderates the permeation of chemical species in contact with it. This interface may be molecularly homogeneous, that is, completely uniform in structure (dense membrane), or it may be chemically or physically heterogeneous, for example containing voids, holes or pores of finite dimensions (porous membrane). A membrane generally has an outer surface and inner surfaces inside pores with which chemical species come in contact.

The weight average molecular weight ($M_w$) and the number average molecular weight ($M_n$) can be estimated by gel-permeation chromatography (GPC) using ASTM D5296 calibrated with polystyrene standards. The polydispersity index (PDI) is hereby expressed as the ratio of weight average molecular weight ($M_w$) to number average molecular weight ($M_n$).

In the present specification, the choice of an element from a group of elements also explicitly describes:

- the choice of two or the choice of several elements from the group,
- the choice of an element from a subgroup of elements consisting of the group of elements from which one or more elements have been removed.

In the passages of the present specification which will follow, any description, even though described in relation to a specific embodiment, is applicable to and interchangeable with other embodiments of the present disclosure. Each embodiment thus defined may be combined with another embodiment, unless otherwise indicated or clearly incompatible. In addition, it should be understood that the elements and/or the characteristics of a composition, a product or article, a process or a use, described in the present specification, may be combined in all possible ways with the other elements and/or characteristics of the composition, product or article, process or use, explicitly or implicitly, this being done without departing from the scope of the present description.

In the present specification, the description of a range of values for a variable, defined by a bottom limit, or a top limit, or by a bottom limit and a top limit, also comprises the embodiments where the variable is chosen, respectively, within the range of values: excluding the bottom limit, or excluding the top limit, or excluding the bottom limit and the top limit. Any recitation herein of numerical ranges by endpoints includes all numbers subsumed within the recited ranges as well as the endpoints of the range and equivalents.

The term “comprising” includes “consisting essentially of” and also “consisting of”.

The use of the singular ‘a’ or ‘one’ herein includes the plural unless specifically stated otherwise.

In addition, if the term “approximately”, “about” or “ca.” is used before a quantitative value, the present teachings also include the specific quantitative value itself, unless specifically stated otherwise. As used herein, the term “approximately”, “about” or “ca.” refers to a +−10% variation from the nominal value unless specifically stated otherwise.

The disclosure of all patent applications, and publications cited herein are hereby incorporated by reference, to the extent that they provide exemplary, procedural or other details supplementary to those set forth herein. Should the disclosure of any patents, patent applications, and publications which are incorporated herein by reference conflict with the description of the present application to the extent that it may render a term unclear, the present description shall take precedence.

DETAILED DESCRIPTION OF PREFERRED EMBODIMENTS

Copolymer (P2)

The copolymer (P2) according to preferred embodiments comprises the recurring units ($R_{P2}$) of the formula (M) and recurring units ($R^*_{P2}$) of the formula (Q), described herein.

In preferred embodiments, the molar ratio of recurring units ($R_{P2}$)/recurring units ($R^*_{P2}$) may be from 0.01/100 to 100/0.01, or from 1/100 to 100/1, or from 1/1 to 20/1 or from 1/1 to 15/1, or preferably from 4/1 to 15/1.

In some embodiments, the copolymer (P2) may also comprise recurring units ($R^*_{P1}$) of the formula (N).

In some embodiments, the copolymer (P2) may also comprise bioactive compound-bound end-groups, hydroxyl end-groups, amine end-groups and/or acid end-groups, preferably bioactive compound-bound and/or amine end-groups.

The copolymer (P2) of the present invention may comprise at least 50 mol. %, or at least 55 mol. %, or at least 60 mol. %, or at least 65 mol. %, or at least 70 mol. %, or at least 75 mol. %, or at least 75 mol. %, or at least 80 mol. % or at least 85 mol. %, or at least 90 mol. %, of recurring units ($R_{P2}$) of formula (M), based on the total number of moles of recurring units in the copolymer (P2).

In preferred embodiments, the copolymer (P2) may comprise collectively at least 50 mol. %, or at least 60 mol. %, or at least 70 mol. %, or at least 80 mol. %, or at least 90 mol. %, or at least 95 mol. %, or at least 99 mol. % of recurring units ($R_{P2}$), ($R^*_{P2}$) and optionally ($R^*_{P1}$), based on the total number of moles of recurring units in the copolymer (P2).

The copolymer (P2) may even preferably consists essentially of recurring units ($R_{P2}$), ($R^*_{P2}$) and optionally ($R^*_{P1}$).

The copolymer (P2) may have a $M_w$ of from 20 000 g/mol to 200 000 g/mol, with a preferred molecular weight from 65,000 to 85,000 g/mol.

The copolymer (P2) may have a polydispersity index of 2 to 4.5, with a preferred PDI of 2 to 3.6.

The copolymer (P2) may be in the form of powder, prills or "soft pellets before being used for the preparation of articles or polymer solutions such as membrane dope solutions.

The copolymer (P2) may be dried to remove moisture before being used for the preparation of articles or polymer solutions/slurries.

Recurring Units ($R_{p2}$)

The recurring units ($R_{P2}$) in copolymer (P2) is of the formula (M), wherein each $R_1$, i, and T were previously described above.

In some embodiments, the copolymer (P2) is such that T in recurring units ($R_{P2}$) is selected from the group consisting of a bond, $-SO_2-$, $-C(CH_3)_2-$ and a mixture therefrom. The copolymer (P2) of the present invention may, for example, comprise recurring units ($R_{P2}$) in which T is $-C(CH_3)_2-$ and also recurring units ($R_{P2}$) in which T is $-SO_2-$.

In some embodiments, the copolymer (P2) is such that each $R_1$ is independently selected from the group consisting of a C1-C12 moiety optionally comprising one or more than one heteroatoms; sulfonic acid and sulfonate groups; phosphonic acid and phosphonate groups; amine and quaternary ammonium groups.

In some embodiments, the copolymer (P2) is such that i is zero for each $R_1$ of recurring units ($R_{P2}$).

In some embodiments, the copolymer (P2) is a bioactive compound-functionalized PSU, PES, or PPSU copolymer, in which the recurring units ($R_{P2}$) have at least one formula selected from formulae (M1), (M2) or (M3):

(M1)

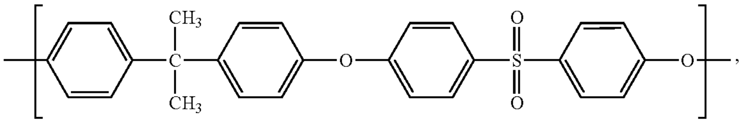

(M2)

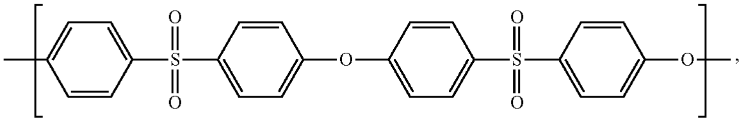

(M3)

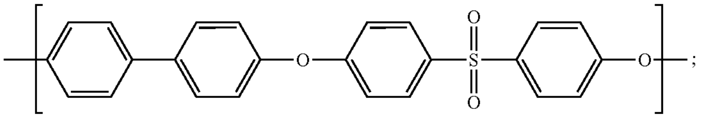

preferably, a formula selected from formulae (M1) and/or (M2).

In preferred embodiments, the copolymer (P2) is a heparin-functionalized PSU, PES, or PPSU copolymer, in which the recurring units ($R_{P2}$) have at least one formula selected from formulae (M1), (M2) or (M3), preferably have a formula selected from formulae (M1) and/or (M2).

Recurring Units ($R^*_{p2}$)

The recurring units ($R^*_{P2}$) in copolymer (P2) are of the formula (Q)

wherein each $R_1$ and i are defined in the same manner as for recurring units ($R_{P2}$);

$G_Q$ is at least one formula selected from the formulae ($G_{Q1}$), ($G_{Q2}$), ($G_{Q3}$), ($G_{Q4}$), ($G_{Q5}$), or ($G_{Q6}$) as described earlier, wherein each k is an integer independently selected from 0 to 4;

each j is an integer independently selected from 2 to 7;

W is a bond, $-C(CH_3)_2-$ or $-SO_2-$, preferably $-C(CH_3)_2-$ or $-SO_2-$, more preferably $-C(CH_3)_2-$;

$R_2$ is represented by the following formula: $-(CH_2)_p-NR_cB$, with p being selected from 1 to 5, with $R_c$ being independently a C1-C6 alkyl or H, and with B representing a bioactive compound which is covalenty and/or ionically bound to $R_2$, preferably bound to the nitrogen atom in $R_2$.

In some embodiments, i is zero for each $R_1$ of recurring units ($R^*_{P2}$).

In some embodiments, k is 0 and j is 3 in recurring units ($R^*_{P2}$).

In some embodiments, $G_Q$ is at least one formula selected from the following formulae ($G'_{Q1}$), ($G'_{Q2}$), ($G'_{Q3}$), ($G'_{Q4}$), ($G'_{Q5}$), or ($G'_{Q6}$):

($G'_{Q1}$)

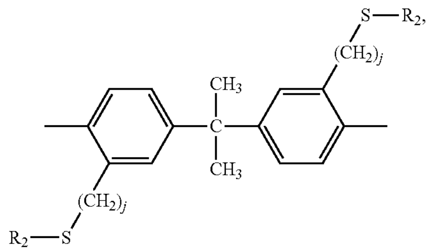

($G'_{Q2}$)

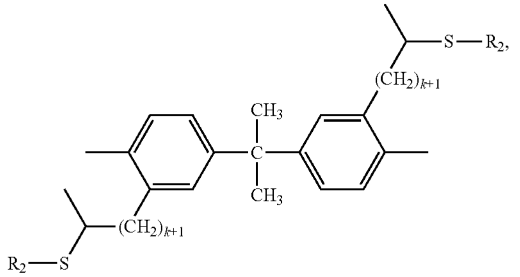

-continued ($G'_{Q3}$)

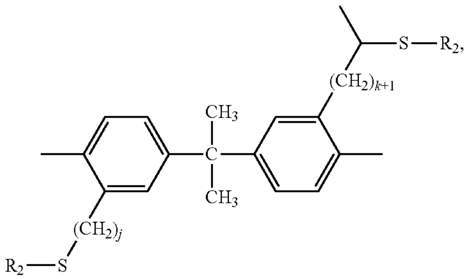

($G'_{Q4}$)

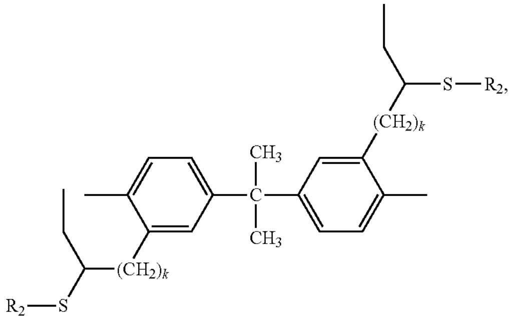

($G'_{Q5}$)

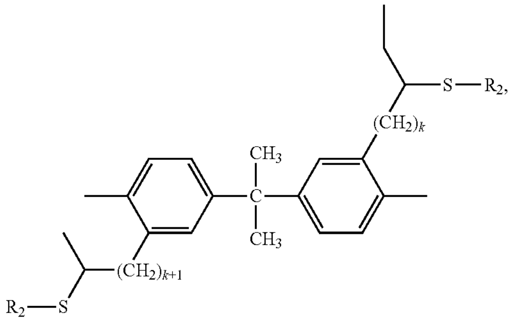

($G'_{Q6}$)

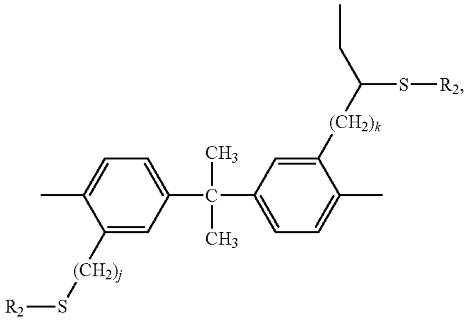

wherein each k, j and $R_2$ are defined the same as in formulae ($G_{Q1}$), ($G_{Q2}$), ($G_{Q3}$), ($G_{Q4}$), ($G_{Q5}$), ($G_{Q6}$).

In some embodiments, $R_2$ is $-(CH_2)_2-NHB$.

Non-limiting examples of bioactive compounds or derivatives thereof "B" suitable for the present invention include:

anti-thrombotic agents, such as heparin or derivative thereof (e.g., salt), amino acids, nucleic acids, such as, but not limited to, deoxyribonucleic acid (DNA), ribonucleic acid (RNA), e.g., messenger RNA (mRNA), glucuronic acid residues, hyaluronic acid or derivatives thereof, proteins, like collagen, keratin, enzymes, such as, but not limited to, lactase;
glucanohydrolases, e.g., alpha-amylase and isoamylase;
pectinases for pectin hydrolysis;
enzymes for high-fructose corn syrup production;
enzymes for debittering of fruit juices, e.g., for removing naringin (responsible for immediate bitterness) and/or limonin (responsible for "delayed bitterness");
esterases;
lipases;
acylases;
enzymes that facilitate acidolysis reactions, ester synthesis or ester interchange reactions, transesterification reactions;
enzymes having phospholipase or protease activity, such as pepsin;
metal-chelating and/or protease inhibitor agents, such as ethylene glycol tetraacetic acid (EGTA) and ethylenediaminetetraacetic acid (EDTA);
acidic lipids such as prostaglandins, or
any combinations of two or more thereof.

Preferred bioactive compounds or derivatives thereof "B" are selected from the group consisting of antithrombotic agents or derivatives thereof, such as heparin or salts thereof.

In some embodiments, the copolymer (P2) comprises recurring units ($R_{P2}$) and at least two, or at least three, or at least four, different recurring units ($R^*_{P2}$) selected from formulae ($G_{Q1}$), ($G_{Q2}$), ($G_{Q3}$), ($G_{Q4}$), ($G_{Q5}$) or ($G_{Q6}$) wherein W is a bond, $—C(CH_3)_2—$ or $—SO_2—$, preferably $—C(CH_3)_2—$ or $—SO_2—$, more preferably $—C(CH_3)_2—$.

Recurring Units ($R^*_{P1}$)

The copolymer (P2) may further comprise recurring units ($R^*_{P1}$) of the formula (N), wherein
each $R_1$ and i are the same as for the recurring units ($R^*_{P2}$);
$G_N$ is at least one formula selected from the group consisting of the formulae ($G_{N1}$), ($G_{N2}$), ($G_{N3}$), ($G_{N4}$), ($G_{N5}$) and ($G_{N6}$), as previously described,
wherein
each k is an integer independently selected from 0 to 4;
each j is an integer independently selected from 2 to 7;
W is a bond, $—C(CH_3)_2—$ or $—SO_2—$, preferably $—C(CH_3)_2—$ or $—SO_2—$, more preferably $—C(CH_3)_2—$;
$R_3$ is represented by the following formula: $—(CH_2)_p—NHR_c$, with p being selected from 1 to 5, with Re being independently a C1-C6 alkyl or H; preferably represented by the following formula: $—(CH_2)_p—NH_2$; more preferably represented by the following formula: $—(CH_2)_2—NH_2$.

In some embodiments, i is zero for each $R_1$ of recurring units ($R^*_{P1}$).

In some embodiments, k is 0 and j is 3 in recurring units ($R^*_{P1}$).

In some embodiments, $R_3$ is: $—(CH_2)_2—NH_2$.

End-Groups of Copolymer (P2)

End-groups are moieties at respective ends of the copolymer chain.

The copolymer (P2) of the present invention may optionally comprises at least 20 μeq of amine end-groups and/or bioactive compound-attached end-groups, for example at least 50 μeq of these end-groups, at least 80 μeq of these end-groups, at least 100 μeq, at least 150 μeq or even at least 200 μeq of these end-groups. The copolymer (P2) may comprise less than 800 μeq of these end-groups, for example less than 600 μeq.

The bioactive compound bound to some of these end-groups is preferably the same bioactive compound "B" which is bound in the recurring units ($R^*_{P2}$).

Process for Manufacturing the Copolymer (P2)

The second aspect of the present invention relates to a process for manufacturing the copolymer (P2) from the functionalized PAES copolymer (P1) as described herein.

The copolymer (P1) comprises some recurring units with side-chain amine groups. Optionally, the copolymer (P1) may further comprise hydroxyl end-groups, amine end-groups and/or acid end-groups, preferably amine end-groups.

In some embodiments, the process for making the copolymer (P2) comprises: contacting the copolymer (P1) with a bioactive compound or derivative thereof (e.g., salt), optionally in the presence of a coupling agent, in an acidic aqueous solvent to bind the bioactive compound to the copolymer (P1) to make the copolymer (P2).

The acidic aqueous solvent preferably has a pH from 3 to 6, or from 4.2 to 5, or from 4.4 to 4.8.

The acidic aqueous solvent may include an organic acid with a pKa from 2.5 to 5, preferably may include citric acid.

The coupling agent may comprise at least one compound selected from the group consisting of EDC (N-(3-Dimethylaminopropyl)-N'-ethylcarbodiimide hydrochloride), NHS (N-Hydroxy succinimide), 1-[3-(Dimethylamino)propyl]-3-ethylcarbodiimide methiodide, 1-(3-Dimethylaminopropyl)-3-ethylcarbodiimide, which is polymer-bound; HOAt (1-Hydroxy-7-azabenzotriazole), PyBOP (benzotriazol-1-yl-oxytripyrrolidinophosphonium hexafluorophosphate), and PyAOP ((7-Azabenzotriazol-1-yloxy)tripyrrolidinophosphonium hexafluorophosphate).

In some embodiments, the coupling agent may comprise a combination of EDC and NHS. Both are available from Sigma-Aldrich, U.S.A.

The binding of the bioactive compound to the copolymer (P1) to make the copolymer (P2) may be ionic and/or covalent.

Without wishing to be limited by such theory, it is believed that the mechanism of attachment/binding of the bioactive compound, such as heparin, to the side-chain amine groups of recurring units ($R^*_{P1}$) and to the optional amine end-groups of the copolymer (P1) may be:
by way of ionic binding of carboxylic acid groups present in the bioactive compound structure, such as in the glycosaminoglycan structure of heparin, with the amine groups thereby creating ionic bonds between COO groups and $NH^{3+}$ groups, and/or
by way of covalent binding (reacting) $COO^-$ groups with $NH^{3+}$ groups to create —N—CO— bonds.

The contacting step may be carried out at a temperate from 15° C. to 60° C., or from 18° C. to 40° C., or from 20° C. to 37° C.

The contacting step may be carried out for a suitable time from 10 minutes to 2 hours, or from 10 min to 1 hr, or from 10 to 30 minutes, or from 30 to 60 minutes, to bind the bioactive compound (or derivative thereof) to the copolymer (P1). Suitable contact time may vary depending on the initial loading of the bioactive compound (or derivative thereof) in the acidic aqueous solvent.

In this process, the copolymer (P1) is modified into the copolymer (P2), so that the binding of the bioactive compound to the side-chain amine groups and optional amine end-groups of the copolymer (P1) confers a functionalization of the copolymer (P2) for a specific property associated with a biological fluid with which the bioactive compound-immobilized copolymer (P2) will come into contact. On the other end, the copolymer (P1) with side-chain amine groups and optional amine end-groups does not have such property. This specific property of the copolymer (P2) may include hemocompatibility. Hemocompatibility can be measured for example by activated partial thromboplastin time (aPTT) for coagulation of blood plasma.

Copolymer (P1)

In preferred embodiments, the copolymer (P1) comprises recurring units ($R_{P1}$) of the formula (M), and recurring units ($R^*_{P1}$) of the formula (N), both formulae being previously described.

The amine-functionalized PAES copolymer (P1) can be selected from the copolymers described in WO 2020/187684A1 (SOLVAY SPECIALTY POLYMERS USA), incorporated herein by reference.

Because the heparin immobilization to the amine-functionalized PAES copolymer (P1) may be carried out with a sub-stoichiometric amount of the bioactive compound (or derivative thereof) compared to the available amount of $-NHR_c$ group (preferably $-NH_2$ group) on the side chains of copolymer (P1), the resulting copolymer (P2) may further comprise recurring units ($R^*_{P1}$) of the formula (N) originating from the amine-functionalized PAES copolymer (P1).

The copolymer (P1) may optionally comprise at least 20 µeq of amine end-groups and may comprise less than 800 µeq of these end-groups.

In some embodiments, the copolymer (P1) is an amine-functionalized PSU, PES, or PPSU copolymer, comprising recurring units ($R_{P1}$) having a formula selected from formulae (M1), (M2) or (M3), described previously.

In some embodiments, the molar ratio of recurring units ($R_{P1}$)/recurring units ($R^*_{P1}$) in the copolymer (P1) is generally the same as the molar ratio of recurring units ($R_{P2}$)/recurring units ($R^*_{P2}$) in the copolymer (P2).

The copolymer (P1) may have a $M_w$ of from 20 to 200 kDa, preferably from 65 to 85 kDa, and a polydispersity index of 2 to 4.5, preferably of 2 to 3.6.

The copolymer (P1) may be in the form of powder, prills or "soft pellets before being used for the preparation of articles or solutions such as membrane dope solutions. In such case, the copolymer (P2) can be made from copolymer (P1) by contacting the copolymer (P1) with the bioactive compound (or derivative thereof), while (at the same time) or after the article is formed.

The copolymer (P1) may be dried to remove moisture before being used for the preparation of articles or polymer solutions such as membrane dope solutions.

Process for Preparing Copolymer (P1)

The copolymer (P1) can be prepared by various chemical processes, notably by free radical-thermal reaction, by free radical-UV reaction, by base-catalysed reaction or by nucleophilic-catalysed reaction. For example, the copolymer (P1) can be prepared in the same manner as described in WO 2020/187684A1 (SOLVAY SPECIALTY POLYMERS USA) from an allyl/vinylene-functionalized PAES copolymer (P0). The PAES copolymer (P0) is functionalized with side-chain allyl/unsaturated carbon-carbon double bonds functional groups which are reactive and can therefore be used to efficiently modify copolymers.

The copolymer (P0) notably comprises recurring units ($R^*_{P0}$) with 2 pendant allyl/vinylene side-chains, which are reacted with compound $R_3-SH$, wherein $R_3$ is represented by the following formula: $-(CH_2)_p-NHR_c$, with p being selected from 1 to 5, with $R_c$ being independently a C1-C6 alkyl or H, preferably represented by the following formula: $-(CH_2)_p-NH_2$, more preferably represented by the following formula: $-(CH_2)_2-NH_2$.

The amination of allyl/vinylene-modified PAES copolymer (P0) to form copolymer (P1) may be carried out at a temperate from 20° C. to 90° C. or from 40° C. to 80° C., or from 50° C. to 70° C.

The allyl/vinylene-modified PAES copolymer (P0) more precisely comprises:

recurring units ($R_{P0}$) of the formula (M) and recurring units (R*P0) of formula (P):

(P)

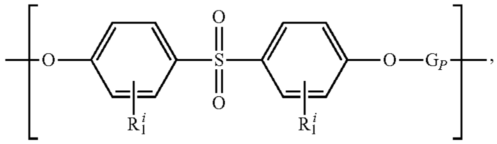

, optionally at least 20 µeq of reactive end-groups, wherein each $R_1$, i and T are defined in the same manner as for recurring units ($R_{P2}$);

$G_P$ is selected from the group consisting of at least one of the following formulae ($GP_1$), ($GP_2$), ($GP_3$):

($G_{P1}$)

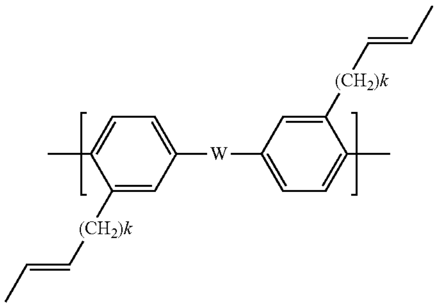

, ($G_{P2}$)

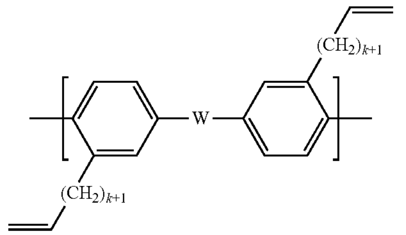

, ($G_{P3}$)

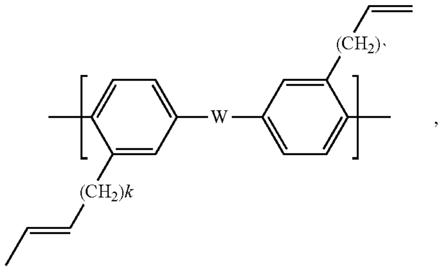

, each k is an integer independently selected from 0 to 4, and W is a bond, $-C(CH_3)_2-$ or $-SO_2-$, preferably $-C(CH_3)_2-$ or $-SO_2-$, more preferably $-C(CH_3)_2-$;

In some embodiments, the copolymer (P0) is such that T in recurring units ($R_{P0}$) is selected from the group consisting of a bond, —$SO_2$—, —$C(CH_3)_2$— and a mixture therefrom. The copolymer (P0) may, for example, comprise recurring units ($R_{P0}$) in which T is —$C(CH_3)_2$— and recurring units ($R_{P0}$) in which T is —$SO_2$.

Because the ethylenic unsaturations are on the side chains of recurring units ($R^*_{P0}$) of copolymer (P0), consequently the copolymer (P1) obtained from copolymer (P0) will contain amine groups in its side chains of the recurring units ($R^*_{P1}$), and the copolymer (P2) obtained from copolymer (P1) will contain bioactive compound-functionalized groups in its side chains of the recurring units ($R^*_{P2}$).

In some embodiments, the copolymer (P0) is an allyl/vinylene-modified PSU, PES, or PPSU copolymer, in which the recurring units ($R_{P0}$) have at least one formula selected from the formulae (M1), (M2) or (M3).

In some embodiments, the molar ratio of recurring units ($R_{P0}$)/recurring units (R*P0) in copolymer (P0) is generally the same as molar ratio of recurring units ($R_{P2}$)/recurring units ($R^*_{P2}$) of copolymer (P2).

The copolymer (P0) may preferably be such that it comprises at least 50 mol. % of recurring units ($R_{P0}$) of formula (M), based on the total number of moles of recurring units in the copolymer (P0), for example at least 55 mol. %, or at least 60 mol. %.

The copolymer (P0) may preferably comprise collectively at least 50 mol. %, or at least 60 mol. %, or at least 70 mol. %, at least 80 mol. %, or at least 90 mol. %, or at least 95 mol. %, or at least 99 mol. % of recurring units ($R_{P0}$) and ($R^*_{P0}$), based on the total number of moles of recurring units in copolymer (P0).

The copolymer (P0) may even preferably consists essentially of recurring units ($R_{P0}$) and (R*P0).

In addition to the allyl/vinylene side-chains, the copolymer (P0) may further comprise reactive end-groups. These reactive end-groups may comprise hydroxyl end-groups, amine end-groups and/or acid end-groups, preferably amine end-groups. The copolymer (P0) may optionally comprise at least 20 μeq of these reactive end-groups and/or less than 800 μeq of these reactive end-groups.

Process for Preparing Copolymer (P0)

The allyl/vinylene-functionalized copolymer (P0) is generally prepared by condensation of at least one aromatic dihydroxy monomer (a1), with at least one aromatic sulfone monomer (a2) comprising at least two halogen substituents and at least one allyl-substituted aromatic dihydroxy monomer (a3).

The condensation to prepare copolymer (P0) is preferably carried out in a solvent (preferably carried out in sulfolane or NMP), in the presence of a base, with molar ratio (a1)+(a3)/(a2) preferably from 0.9 to 1.1, for example from 0.92 to 1.08 or from 0.95 to 1.05. The temperature for the condensation reaction to prepare copolymer (P0) is kept at about 150° C. to about 350° C., preferably from about 210° C. to about 300° C. for about one to 15 hours.

In some embodiments, the monomer (a1) comprises, based on the total weight of the monomer (a1), at least 50 wt. % of 4,4' dihydroxybiphenyl (biphenol), of bisphenol A, and/or of bisphenol S. In some embodiments, the monomer (a1) comprises, based on the total weight of the monomer (a1), at least 60 wt. %, or at least 70 wt. %, or at least 80 wt. %, or at least 90 wt. %, or at least 95 wt. % of biphenol, bisphenol A, bisphenol S, or any mixture thereof. In some embodiments, the monomer (a1) consists essentially of biphenol, or bisphenol A, or bisphenol S, or any mixture thereof.

In some embodiments, the monomer (a2) is a 4,4-dihalosulfone comprising at least one of a 4,4'-dichlorodiphenyl sulfone (DCDPS) or 4,4' difluorodiphenyl sulfone (DFDPS), preferably DCDPS. In some embodiments, the monomer (a2) comprises, based on the total weight of the monomer (a2), at least 60 wt. %, or at least 70 wt. %, or at least 80 wt. %, or at least 90 wt. %, or at least 95 wt. % of DCDPS, DFDPS or any mixture thereof, preferably DCDPS. In some embodiments, the monomer (a2) consists essentially of DCDPS.

In some embodiments, the monomer (a3) comprises, based on the total weight of the monomer (a3), at least 50 wt. % of 2,2'-diallylbisphenol A (daBPA), 2,2'-diallylbisphenol S (daBPS) and/or 2,2'-diallylbiphenol (daBP), preferably daBPA and/or daBPS, more preferably daBPA. In some embodiments, the monomer (a3) comprises, based on the total weight of the monomer (a3), at least 60 wt. %, or at least 70 wt. %, or at least 80 wt. %, or at least 90 wt. %, or at least 95 wt. % of diallybiphenol, daBPA and/or daBPS, preferably daBPA and/or daBPS, more preferably daBPA. In some embodiments, the monomer (a3) consists essentially of daBPA.

More information concerning the condensation conditions for the allyl/vinylene-functionalized copolymer (P0) preparation can be found in WO 2020/187684A1 (SOLVAY SPECIALTY POLYMERS USA), Article Comprising the Copolymer (P2)

Another aspect of the present invention provides an article (preferably a shaped article) comprising the copolymer (P2) according to the present invention.

An article comprising the copolymer (P2) may be selected from the group consisting of medical devices; implants; membranes; coatings; melt processed films, monofilaments and fibers; solution processed films (porous and non-porous films, including solution casted membranes, and membranes from solution spinning); solution processed monofilaments; melt process monofilaments and fibers; hollow fibers and solid fibers; coatings; printed objects, and injection and compression molded objects.

The copolymer (P2) can be incorporated into articles having a polymeric surface. The article can have a polymeric surface, at least a portion of which comes into direct contact with a biological fluid and/or food product in its intended application setting. The polymeric surface may be an external or internal surface of the article. For example, a medical implant has an external surface intended to come into direct contact with a biological fluid, such as blood, plasma or serum. A person of ordinary skill in the art will know which surface is intended to contact a biological fluid or food product based upon the article's intended application setting.

In some embodiments, a surface of an article can comprise the copolymer (P2). For example, the copolymer (P2) can form a portion of such surface, or the copolymer (P2) can form all, or substantially all, of the article.

As another example, a surface of the article can comprise a coating or film comprising the copolymer (P2), disposed on an underlying substrate. In such embodiments, the underlying substrate can be a structural component having a composition distinct from the copolymer (P2).

In embodiments in which the copolymer (P2) is in a film or coating, the film or coating can have an average thickness of from about 25 μm to about 1 mm.

In some embodiment, the shaped article comprising the copolymer (P2) may be a medical device or implants, implantable cardioverter defibrillators, artificial hip joints, artificial knee joints, heart pacemakers, breast implants, spinal fusion hardware (including, but not limited to, artificial discs), intra-uterine devices, artificial knees, stents (including, but not limited to, coronary stents), stent grafts, bypass grafts, ear tubes, prostheses, artificial heart valves, implantable tubes (including, but not limited to, catheters), filtration membranes (including, but not limited to, hemodialysis membranes), surgical instruments (including, but not limited to, forceps, clamps, retractors, distractors, scalpels, surgical scissors, dilators, specula, suction tips, staplers, injection needles, drills, fiber optic instruments; preferably coronary stents, artificial heart valves, or heart pacemakers.

The copolymer (P2) can be included in at least a portion of a surface of the article (e.g., stent) for example in the form of a coating of copolymer (P2) onto a surface of a substrate (e.g., a tubular substrate for a stent), when it is intended for such surface to come in contact with a biological fluid such as blood, plasma, or serum. Alternatively, the copolymer (P2) can form all, or substantially all, of the article (e.g., stent).

A shaped article comprising the copolymer (P2) may be a stent. A stent is generally a tube inserted into the lumen of an anatomic vessel or duct to keep the passageway open.

A shaped article comprising the copolymer (P2) preferably may be a membrane, or a part thereof, being selected from membranes for bioprocessing and medical filtrations (such as hemodialysis membranes), membranes for food and beverage processing, membranes for water purification, membranes for waste water treatment and membranes for industrial process separations involving aqueous media.

Among membranes, the copolymer (P2) according to the present invention is particularly suitable for manufacturing membranes intended for contact with an aqueous media, including a biological fluid, such as blood, or a food product, such as beverages (e.g., fruit juice, milk).

From an architectural perspective, membranes comprising the copolymer (P2) may be provided under the form of flat structures (e.g. films or sheets), corrugated structures (such as corrugated sheets), tubular structures, or hollow fibers; as per the pore size is concerned, full range of membranes (non-porous and porous, including for microfiltration, ultrafiltration, nanofiltration, and reverse osmosis) can be advantageously manufactured with the copolymer (P2) or at the same time as the copolymer (P1) is modified to copolymer (P2); pore distribution can be isotropic or anisotropic.

A shaped article comprising the copolymer (P2) may be, as above mentioned, under the form of films and sheets. These shaped articles are particularly useful as specialized optical films or sheets, and/or suitable for packaging.

Further, a shaped article comprising the copolymer (P2) can be three-dimensional molded parts, in particular transparent or colored parts.

Among applications of use, mention can be made of healthcare applications, in particular medical and dental applications, wherein shaped articles comprising the copolymer (P2) can advantageously be used for replacing metal, glass and other traditional materials in single-use and reusable instruments and devices.

Use of the Copolymer (P2)

Another aspect of the present invention provides the use of the copolymer (P2) for preparing an article (or a part thereof) as described herein.

This aspect may comprise: using the copolymer (P2) in forming the article or a part thereof.

Method for Preparing an Article

Another aspect of the present invention provides a method for preparing an article (or a part thereof) comprising the copolymer (P2). Such method may be carried out in different ways. For example, the method may comprise performing one of the following:

method (a): using the copolymer (P2) in forming the article or part thereof; or method (b): contacting the copolymer (P1) with a bioactive compound or derivative thereof to make the copolymer (P2) while at the same time forming the article or part thereof; or method (c): contacting a pre-formed article or part thereof comprising the copolymer (P1) with the bioactive compound or derivative thereof to make the copolymer (P2), wherein the copolymer (P1) in method (b) or method (c) comprises recurring units ($R_{P1}$) of formula (M), and recurring units ($R^*_{P1}$) of formula (N), as described herein.

In some embodiments when the article is a membrane or a part thereof, the method preferably includes a phase inversion occurring in a liquid phase (e.g., precipitation bath) to form the membrane or part thereof.

The contacting step in method (b) or method (c) may be carried out, optionally in the presence of a coupling agent, in an acidic aqueous solvent, preferably of pH from 3 to 6, or from 4.2 to 5, or from 4.4 to 4.8, to bind the bioactive compound to the copolymer (P1) to make the copolymer (P2).

In some embodiments of method (a), the article may be formed from a solution comprising the copolymer (P2).

In some embodiments, the method (b) may be called the in-situ method, while the method (c) may be called the ex-situ method.

In some embodiments of method (b), the article may be made using the copolymer (P1), the bioactive compound (or derivative thereof), and optionally the coupling agent, in an acidic aqueous solvent, in order to make in-situ the copolymer (P2) at the same time as the article is being formed in order for the bioactive compound to ionically and/or covalently bind to the copolymer (P1), and particularly to the amine side chains and optional amine end-groups of the copolymer (P1), in order to form in-situ the copolymer (P2).

In some embodiments of method (c), the article (or part thereof) may be first pre-formed using the copolymer (P1), and after being pre-formed into a shape, the pre-formed article is placed in contact with the bioactive compound or derivative thereof, and optionally the coupling agent, in an acidic aqueous solvent, in order for the bioactive compound to ionically and/or covalently bind to the copolymer (P1), and particularly to the amine side chains and optional amine end-groups of the copolymer (P1), in order to form ex-situ the copolymer (P2), particularly on the article's surface(s).

In yet other embodiments of the method for preparing an article (or part thereof) comprising the copolymer (P2), the immobilisation of one or more bioactive compounds may be carried in two (consecutive) steps in a method (d):

1/ immobilisation of at least one (first) bioactive compound onto copolymer (P1) to make copolymer (P2) before or while forming the article; and 2/ immobilisation of at least a (second) bioactive compound—same or different as the bioactive compound used in step 1/—onto the copolymer (P2) now present in the article to form a copolymer (P2').

Preferably, at least a same bioactive compound is used in these two immobilisation steps 1/and 2/.

The difference between copolymers (P2) and (P2') is the amount of bioactive compound bound to the copolymer structure and the amount of amine groups remaining in the copolymer structure.

Preferably, the immobilisation step 1/in method (d) is done with a sub-stoichiometric molar amount of the (first) bioactive compound relative to the molar amount of amine groups (in side chains and/or end-groups) of copolymer (P1) so as to retain some 'unbound' or 'free' amine groups, which then can serve as binding sites for the (second) bioactive compound used in the immobilisation step 2/.

In some instances of method (d), the immobilisation step 1/may be carried out to ionically bind a (first) bioactive compound, while the immobilisation step 2/may be carried out to covalently bind a (second) bioactive compound-same or different as the bioactive compound used in step 1/, or vice versa.

Yet in other instances of method (d), the immobilisation step 1/may be carried out before or while forming the article with a coupling agent in order to covalently bind a (first) bioactive compound onto copolymer (P1) to make copolymer (P2), while the immobilisation step 2/may be carried out, after forming the article, without a coupling agent in order to ionically bind a (second) bioactive compound (same or different as first bioactive compound in the immobilisation step 2/) onto the copolymer (P2) to make a copolymer (P2').

Membrane or Film (as Article)

In some embodiments, the article made as described above may be a film or a membrane, or a part thereof.

A particular embodiment of an article (preferably a shaped article) relates to a membrane comprising the copolymer (P2). The membrane may be used for purifying water, a food product, or a biological fluid, such as blood.

According to the present invention, a membrane is typically a microporous membrane which can be characterized by its average pore diameter and porosity, i.e., the fraction of the total membrane that is porous.

The membrane may have a gravimetric porosity (%) of 20 to 90% and comprises pores, wherein at least 90% by volume of the said pores has an average pore diameter of less than 5 μm. Gravimetric porosity of the membrane is defined as the volume of the pores divided by the total volume of the membrane.

Membranes having a uniform structure throughout their thickness are generally known as symmetrical membranes; membranes having pores which are not homogeneously distributed throughout their thickness are generally known as asymmetric membranes. Asymmetric membranes are characterized by a thin selective layer (0.1-1 μm thick) and a highly porous thick layer (100-200 μm thick) which acts as a support and has little effect on the separation characteristics of the membrane.

Membranes can be in the form of a flat sheet or in the form of tubes.

A membrane may be formed using a plurality of films.

Tubular membranes are classified based on their dimensions in tubular membranes having a diameter greater than 3 mm; capillary membranes, having a diameter comprised between 0.5 mm and 3 mm; and hollow fibers having a diameter of less than 0.5 mm. Capillary membranes are otherwise referred to as hollow fibers.

Hollow fibers are particularly advantageous in applications where compact modules with high surface areas are required.

The membrane according to the present invention can be manufactured using any of the conventionally known membrane preparation methods, for example, by a solution casting or solution spinning method.

The membrane according to the present invention may be prepared by a phase inversion method occurring in a liquid phase, said method comprising the following steps:

(i) preparing a polymer solution comprising the copolymer (P1) or (P2) described herein and a polar solvent,
(ii) processing said polymer solution into a film; and
(iii) contacting said film with a non-solvent bath.

Various embodiments of the method for making an article described herein (e.g., methods (a), (b), (c), (d)) are equally applicable to make the film or membrane.

In particular embodiments, the film or membrane may be first made using the copolymer (P1), and after being preformed, the pre-formed film or membrane comprising the copolymer (P1) is placed in contact with the bioactive compound (or derivative thereof), and optionally the coupling agent, in an acidic aqueous solvent, in order for the bioactive compound to ionically and/or covalently bind to the copolymer (P1), and particularly to the amine side chains and optional amine end-groups of the copolymer (P1), in order to form ex-situ the copolymer (P2) on the membrane or film, particularly on (inner and outer) surfaces of the membrane or film.

In yet other embodiments, the immobilisation of one or more bioactive compounds onto a film or membrane may be carried in two successive immobilization steps as described herein in relation to methods for forming the article.

The membrane or film may further comprise at least one polymer distinct from the copolymer (P2) described herein. For example the membrane or film may further comprise at least one polymer selected from the group consisting of the copolymer (P1), another sulfone polymer, e.g., polysulfone (PSU), polyethersulfone (PES), poly(biphenyl ether sulfone) (PPSU), a polyphenylene sulfide (PPS), a poly(aryl ether ketone) (PAEK), e.g. a poly(ether ether ketone) (PEEK), a poly(ether ketone ketone) (PEKK), a poly(ether ketone) (PEK) or a copolymer of PEEK and poly(diphenyl ether ketone) (PEEK-PEDEK copolymer), a polylactide (PLA), a polyetherimide (PEI), a polycarbonate (PC), a polyphenylene oxide (PPO), polyvinylpyrrolidone (PVP) and/or polyethylene glycol (PEG).

In some embodiments, the membrane or film may further comprise at least another sulfone polymer distinct from the copolymer (P2), e.g., may comprise at least one polymer selected from the group consisting of the copolymer (P1), PSU, PES, PPSU, PC, PPO, PEI, PLA, PVP and/or PEG, said PEG preferably having a molecular weight of at least 200.

The membrane or film may comprise the copolymer (P2) described herein in an amount of at least 1 wt. %, or at least 2 wt. %, at least 3 wt. %, at least 4 wt. %, at least 5 wt. %, at least 6 wt. %, or at least 7 wt. %, or at least 8 wt. %, based on the total weight of the polymers, and/or may comprise the copolymer (P2) described herein in an amount of more than 50 wt. %, for example more than 55 wt. %, more than 60 wt. %, more than 65 wt. %, more than 70 wt. %, more than 75 wt. %, more than 80 wt. %, more than 85 wt. %, more than 90 wt. %, more than 92 wt. %, or more than 95 wt. %, based on the total weight of the polymers.

According to an embodiment, the membrane or film may comprise the copolymer (P2) and optionally another sulfone polymer distinct from the copolymer (P2), e.g., the copolymer (P1), PSU, PES, PPSU described herein, in an amount ranging from 1 to 99 wt. %, for example from 2 to 98 wt. %, from 3 to 97 wt. % or from 4 to 96 wt. %, based on the total weight of polymers.

The membrane or film may further comprise at least one non-polymeric ingredient such as a solvent, a filler, a lubricant, a mold release, an antistatic agent, a flame retardant, an anti-fogging agent, a matting agent, a pigment, a dye and an optical brightener.

A suitable example of a method for forming a membrane from a polyaryl ether sulfone polymer is described in US2019/054429A1 (Solvay Specialty Polymers USA), incorporated herein by reference.

Polymer Solution (SP) for Preparing a Membrane

Another aspect of the present invention is directed to a polymer solution/slurry (SP) for preparing a membrane, which comprises the copolymer (P1) or (P2) in a polar organic solvent [solvent ($S_{SP}$)].

The polymer solution/slurry (SP) is preferably a polymer solution.

SP may further comprise at least one additional polymer distinct from the copolymer (P1) or (P2) described herein, for example another sulfone polymer, e.g., PSU, PES, PPSU; a PPS; a PAEK, e.g., PEEK, PEKK, PEK or a PEEK-PEDEK copolymer; PPO; PLA; PEI; PC; PVP; and/or PEG.

SP may particularly contain PVP and/or PEG having a molecular weight of at least 200, as pore forming agents.

The overall concentration of copolymer (P1) and/or copolymer (P2) and optional additional polymer(s) in SP may be at least 8 wt. %, or preferably at least wt. %, based on the total SP weight and/or is at most 70 wt. %; or at most 60 wt. %; or at most 50 wt. %; or at most 40 wt. %; or at most 30 wt. %, based on the total SP weight. Concentrations of all polymers in SP ranging between 10 and 25% wt, and more preferably between 10 and 22% wt, based on the total SP weight are particularly advantageous.

The concentration of the solvent ($S_{SP}$) in SP may be at least 20 wt. %, preferably at least 30 wt. %, based on the total SP weight and/or is at most 70 wt. %; preferably, at most 65 wt. %; more preferably, at most 60 wt. %, based on the total SP weight.

The solvent ($S_{SP}$) in SP may be selected from a group consisting of 1,3-dimethyl-2-imidazolidinone (DMI), dimethylsulfoxide (DMSO), dimethylsulfone (DMSO2), diphenylsulfone, diethylsulfoxide, diethylsulfone, diisopropylsulfone, tetrahydrothiophene-1,1-dioxide (commonly called tetramethylene sulfone or sulfolane), N-Methyl-2-pyrrolidone (NMP), N-butylpyrrolidinone (NBP), N-ethylpyrrolidone (NEP), N,N'-dimethylacetamide (DMAc), N,N'-dimethylpropyleneurea (DMPU), dimethylformamide (DMF), tetrahydrothiophene-1-monoxide, and mixtures thereof. Preferably the solvent ($S_{SP}$) in SP is N,N'-dimethylacetamide (DMAc), particularly suitable for preparing membranes or films.

Exemplary solvents ($S_{SP}$) which may be used, alone or in combination, in SP are described in patent applications in US2019/054429A1 (Solvay Specialty Polymers Italy), in particular solvents described in paragraphs [0057]-[0129], and WO 2019/048652 (Solvay Specialty Polymers USA), incorporated herein by reference.

The SP may contain additional components, such as nucleating agents, fillers and the like.

Purification Method for a Biological Fluid

A further aspect of the present invention may be directed to a purification method comprises at least a filtration step through the membrane or film comprising the copolymer (P2) described herein.

Preferably, the purification method is for purifying a human biological fluid, preferably a blood product, such as whole blood, plasma, fractionated blood components or mixtures thereof, that is carried out in an extracorporeal circuit. The extracorporeal circuit for carrying out a method comprises at least one filtering device (or filter) comprising at least one membrane or film as described above.

As intended herein, a blood purification method through an extracorporeal circuit comprises hemodialysis (FD) by diffusion, hemofiltration (HF), hemodyafiltration (HDF) and hemoconcentration. In HF, blood is filtered by ultrafiltration, while in HDF blood is filtered by a combination of FD and HF.

Blood purification methods through an extracorporeal circuit are typically carried out by means of a hemodialyzer, i.e. equipment designed to implement any one of FD, HF or HFD. In such methods, blood is filtered from waste solutes and fluids, like urea, potassium, creatinine and uric acid, thereby providing waste solutes- and fluids-free blood.

Typically, a hemodialyzer for carrying out a blood purification method comprises a cylindrical bundle of hollow fibers of membranes, said bundle having two ends, each of them being anchored into a so-called potting compound, which is usually a polymeric material acting as a glue which keeps the bundle ends together. Potting compounds are known in the art and include notably polyurethanes. By applying a pressure gradient, blood is pumped through the bundle of membranes via the blood ports and the filtration product (the "dialysate") is pumped through the space surrounding the filers.

EXAMPLES

The invention will be now described in more details with reference to the following examples, whose purpose is merely illustrative and not intended to limit the scope of the invention.

Raw Materials

DCDPS (4,4'-dichlorodiphenyl sulfone), available from Solvay Speciality Polymers BPA (bisphenol A), available from Covestro, U.S.A.

BPS (bisphenol S), available from Nicca Chemical company daBPA (2,2'-diallyl Bisphenol), available from Sigma-Aldrich, U.S.A.

$K_2CO_3$ (Potassium Carbonate), available from Armand products $NaHCO_3$(Sodium bicarbonate), available from Solvay SA, France NMP (2-methyl pyrrolidone), available from Sigma-Aldrich, U.S.A.

Cysteamine hydrochloride available from Sigma-Aldrich, U.S.A.

3-Aminophenol available from Sigma-Aldrich, U.S.A.

ADVN 2,2'-Azobis (2,4 dimethylvaleronitrile) available from Miller-Stephenson Chemical Co., Inc.

Heparin sodium, available from BOC sciences, U.S.A.

EDC (N-(3-Dimethylaminopropyl)-N'-ethylcarbodiimide hydrochloride), available from Sigma-Aldrich, U.S.A.

NHS (N-Hydroxy succinimide) available from Sigma-Aldrich, U.S.A.

Citric acid, available from Sigma-Aldrich, U.S.A.

$NaHPO_4$, available from Sigma-Aldrich, U.S.A.

Toluidene blue, available from Sigma-Aldrich, U.S.A.

Test Methods

GPC—Molecular Weight (Mn, Mw)

The molecular weights (Mn, Mw) were measured by gel permeation chromatography (GPC), using methylene chloride as a mobile phase. Two 5μ mixed D columns with guard column from Agilent Technologies were used for separation. An ultraviolet detector of 254 nm was used to obtain the chromatogram. A flow rate of 1.5 ml/min and injection volume of 20 μL of a 0.2 w/v % solution in mobile phase was selected. Calibration was performed with 12 narrow molecular weight polystyrene standards (Peak molecular weight range: 371,000 to 580 g/mol).

Thermal Gravimetric Analysis (TGA)

TGA experiments were carried out using a TA Instrument TGA Q500. TGA measurements were obtained by heating the sample at a heating rate of 10° C./min from 20° C. to 800° C. under nitrogen.

$^1$H NMR $^1$H NMR spectra were measured using a 400 MHz Bruker spectrometer with TCE or DMSO as the deuterated solvent. All spectra are reference to residual proton in the solvent.

DSC

DSC was used to determine glass transition temperatures (Tg) and melting points (Tm)—if present. DSC experiments were carried out using a TA Instrument Q100. DSC curves were recorded by heating, cooling, re-heating, and then re-cooling the sample between 25° C. and 320° C. at a heating and cooling rate of 20° C./min. All DSC measurements were taken under a nitrogen purge. The reported Tg and Tm values were provided using the second heat curve unless otherwise noted.

Amine Content Estimation

A sample of 0.2 to 0.3 g of polymer was dissolved in 55 mL of methylene chloride with stirring. 15 mL of glacial acetic acid was added. The sample was then titrated potentionmetrically with 0.1N perchloric acid in acetic acid using a Metrohm Titrando 809 Titrator with a Metrohm Solvotrode electrode. Perchloric acid titrant reacts with basic groups in the sample and produces an endpoint in the potential curve when all base has been neutralized. Two blanks and one control sample were tested prior to testing samples. Two replicates were run for each sample. The results were reported only after duplicate analyses agree within 5% for base concentration values above 100 μeq/g or were within 10 μeq/g for values below 100 μeq/g.

Calculation of base concentration:

$$[\text{Sample Base, } \mu\text{eq/g}]=(N \text{ perchloric acid})\times(V \text{ perchloric acid}-V \text{ blank})\times 1000/W \text{ Sample}$$

N perchloric acid=number of moles of perchloric acid (N)

V perchloric acid=volume of perchloric acid (mL)

V blank=volume of blank (mL)

W sample=weight of the sample (g)

The blank value was determined from the volume of titrant needed to achieve the same mV electrode potential as the sample titration endpoint potential.

Example 1

I. Preparation of Allyl/Vinylene-Modified PSU Copolymer (P0-A)

The allyl/vinylene-modified PSU copolymer (P0-A) was prepared according to Scheme 1 described in WO 2020/187684A1 (SOLVAY SPECIALTY POLYMERS USA), incorporated herein by reference.

The copolymerization took place in a glass reactor vessel (2 L) fitted with an overhead stirrer, nitrogen inlet and an overhead distillation set-up. The monomers: 4,4'-dichlorodiphenyl sulfone (201.01 g), Bisphenol A (145.42) and 2,2'-diallyl Bisphenol A (19.9 g) were added to the vessel first, followed by the addition of potassium carbonate (105.45 g) and NMP (464 g). The resulting reaction mixture was heated from room temperature to 190° C. using a 1° C./min heating ramp. The reaction was terminated by stopping the heating. The reaction mixture was filtered, coagulated into methanol and dried at 110° C.

The copolymer was in the form of a racemate product. Due to the presence of the base and high temperature during polymerization, the 2,2'-diallyl bisphenol monomer racemized during polymerization in such a way that the position of the double bond changed along the side chains. This led to the formation of molecules differing from each other's by the fact that the double bond may be at the end of the side chain or one carbon before the end of the side chain, as shown in Scheme 1 described in WO 2020/187684A1.

Characterization of Allyl/Vinylene-Modified PSU Copolymer (P0-A)

GPC: Mn=29321 g/mol; Mw=144711 g/mol; PDI=4.94

$^1$H NMR: The presence of unsaturated groups was confirmed by the appearance of a multiplet at 6.1-6.4 ppm which indicates the incorporation of the 2,2'-diallyl BPA monomer in the polymer.

II. Preparation of Amine-Functionalized PSU Copolymer (P1-A)

The amine-functionalized PSU copolymer (P1-A) was prepared according to Scheme 7 described in WO 2020/187684A1 (SOLVAY SPECIALTY POLYMERS USA), incorporated herein by reference, except that the reaction mixture contained ADVN (instead of AIBN) and the reaction was carried out in NMP at 50° C. (instead of 70° C.).

The amine functionalization took place in a glass reactor vessel (1 L) fitted with an overhead stirrer, nitrogen inlet. The allyl/vinylene-modified PSU copolymer (P0-A) (122.3 g), cysteamine hydrochloride (56 g) were dissolved at room temperature in NMP (877 g). The reaction mixture was purged with $N_2$ for at least 45 minutes, then the reaction was heated to 50° C. and ADVN (2,2'-azobis(2,4-dimethylvaleronitrile) (12.35 g) was added. The reaction was allowed to proceed for 12 hours, after which the heating was stopped. The reaction mixture was then coagulated in 3000 mL water in which 50 g of $K_2CO_3$ were added. The coagulated polymer was then washed with water (3000 mL), washed twice with methanol (3000 mL) and then dried at 110° C.

Characterization of Amine Functionalized PSU Copolymer (P1-A)

GPC: Mn=7368 g/mol, Mw=30406 g/mol, PDI=4.13

Amine groups: 381 μeq/g $^1$H NMR: The conversion of unsaturated groups was confirmed by the disappearance of a multiplet at 6.1-6.4 ppm which indicates the incorporation of the side-chain amino groups in the polymer.

IV. Preparation of Heparin-Functionalized PSU Copolymer (P2-A)

The heparin-functionalized PSU copolymer (P2-A) can be prepared according to the scheme illustrated in FIG. 1. In this scheme, the PSU copolymer (P1) is illustrated with recurring units ($R_{P1}$) of formula (M1) and recurring units ($R^*_{P1}$) of formula (N) with $G_N$=$G_{N6}$ (k=0, j=2) and $R_3$=—$(CH_2)_2$—$NH_2$.

Example 2

V. Preparation of Allyl/Vinylene-Modified PES Copolymer (P0-B)

An allyl/vinylene-modified PES copolymer (P0-B) was prepared according to Scheme 3 described in WO 2020/187684A1 (SOLVAY SPECIALTY POLYMERS USA), except that the reaction was carried out in sulfolane (instead of NMP) at 210° C. (instead of 190° C.).

The copolymerization took place in a glass reactor vessel (2 L) fitted with an overhead stirrer, nitrogen inlet and an overhead distillation set-up. The monomers: 4,4'-dichlorodiphenyl sulfone (145 g), bisphenol S (113.8 g) and 2,2'-diallyl Bisphenol (13.87 g) were added to the vessel first, followed by the addition of potassium carbonate (71.17 g) and sulfolane (431 g). The reaction mixture was heated from room temperature to 210° C. using a 1° C./min heating ramp. The reaction was terminated by stopping the heating. The reaction mixture was filtered, coagulated into methanol and dried at 110° C.

The copolymer was in the form of a racemate product. Due to the presence of the base and high temperature during polymerization, the 2,2'-diallyl bisphenol monomer racemized during polymerization in such a way that the position of the double bond changed along the side chains. This led to the formation of molecules differing from each other's by the fact that the double bond could be at the end of the side chain or one carbon before the end of the side chain, as in Scheme 3.

Characterization of Allyl/Vinylene-Modified PES Copolymer (P0-B)

GPC: Mn=19720 g/mol; Mw=60788 g/mol; PDI=3.08

DSC: 135° C.

TGA: 430° C.

$^1$H NMR: The presence of unsaturated groups was confirmed by the appearance of a multiplet at 6.1-6.4 ppm which indicates the incorporation of the 2,2'-diallyl BPA monomer in the polymer.

VI. Preparation of Amine-Functionalized PES Copolymer (P1-B)

The amine-functionalized PSU copolymer (P1-B) was prepared from the allyl/vinylene-modified PES copolymer (P0-B) according to Scheme 7 described in WO 2020/187684A1 (SOLVAY SPECIALTY POLYMERS USA), except that the reaction mixture contained ADVN (instead of AIBN) and the reaction was carried out in NMP at 50° C. (instead of 70° C.).

The amine functionalization took place in a glass reactor vessel (1 L) fitted with an overhead stirrer, nitrogen inlet. The allyl/vinylene-modified PES copolymer (P0-B) reaction solution (200 g), cysteamine hydrochloride (6.64 g) were purged with $N_2$ for at least 45 minutes, then the reaction was heated to 50° C. and ADVN (4.81 g) was added. The reaction was allowed to proceed for 12 hours, after which the heating was stopped. The reaction mixture was then coagulated in 3000 mL water in which 50 g of $K_2CO_3$ were added. The coagulated polymer was then washed with water (3000 mL), washed twice with methanol (3000 mL) and then dried at 110° C.

Characterization of Amine Functionalized PES Copolymer (P1-B)

GPC: Mn=3876 g/mol; Mw=11855 g/mol; PDI=3.06

Amine groups: 381 μeq/g

VII. Preparation of Heparin-Functionalized PES Copolymer (P2-B)

The heparin-functionalized PES copolymer (P2-B) can be prepared from an amine-functionalized PSU copolymer (P1-B) similarly to the scheme illustrated in FIG. 1.

Example 3

Casting/Heparinization of Membrane Via In-Situ Method (b)

A series of membranes comprising heparin-functionalized PSU copolymers were cast from samples of amine-functionalized PSU copolymer (P1-A) in the presence of heparin sodium salt via the so-called in-situ "method (b)" using a phase inversion protocol.

Preparation of Heparin-Containing Solution

A heparin-containing solution was prepared and it contained:

- N,N dimethylacetamide (DMAc);
- a buffer stock solution of pH 4.6 containing $Na_2HPO_4$ and citric acid;
- a heparin salt stock solution (containing 0.45 g heparin sodium salt in 299.55 g deionized water);
- water;
- optionally a coupling agent stock solution (containing 0.09 g EDC and 0.09 g NHS in 299.82 g water).

The conditions for phase inversion protocol are provided in Table 1.

TABLE 1

| | | Conditions | |
|---|---|---|---|
| | | Ionically binding | Covalently binding |
| | Water | 375 | 325 |
| Solvent | DMAC | 25 | 25 |
| Buffer stock solution | $Na_2HPO_4$ Citric acid | 50 | 50 |
| Heparin stock solution | Heparin sodium | 50 | 50 |
| Coupling agent stock solution | EDC + NHS | — | 50 |
| Precipitation bath | Total (g) | 500 | 500 |

For covalently binding heparin salt to the amine-functionalized PSU copolymer (P1-A), a coupling agent (EDC+NHS) in the form of the stock solution was used, while for ionic binding, the coupling agent was omitted.

The use of stock solutions for the buffer, heparin salt and coupling agent, easily allowed the study of the effect of buffer, heparin and coupling agent contents. The amounts (weights) of buffer, heparin and coupling agent could be varied, and then the water amount could be adjusted to achieve a constant precipitation bath volume for all of the membranes prepared.

Polymer Dope Solution

Amine-functionalized PSU copolymers (P1-A) made according to the procedure provided in Example 1 were used as substrates to attach heparin either by ionic bond or covalent bond.

Polymer solutions (10% w/w PSU copolymers (P1-A) in DMAc) were filtered through a 2.7-micron glass fiber filter before casting membranes. The filtrate should be clear, bright solution, with no evidence of particulate contamination. The filtrate, like the original polymer solution may be colored.

Precipitation Bath

A fresh precipitation bath (5% w/w DMAc in deionized water (final concentration)) was used for the formation of each membrane.

Casting of Dope Solution

Membranes were cast, at room temperature, by hand using a 6 mil draw bar with glass plates (10"×6"×¼"). The glass plates were stored in deionized water, and were damped dry prior to casting a film. Typically, approximately 3 g (target range: 2.75-3.25 g) of the dope polymer solution were cast; this resulted in a >90% usage of polymer solution, i.e. >90% of the polymer solution was in the form of the membrane, and the remainder was wastage (stuck to the draw bar).

Formation and Washing of Porous Membrane

The precipitation bath (500 g of 5% w/w DMAc in deionized water as precipitation medium) was prepared within 1-2 hours of immersion of the cast membrane. A clean polypropylene storage box (nominal 1 gallon capacity, 13"×8"×5") was used as the precipitation bath container.

The glass plate with the cast dope polymer solution (3 g) spread on its surface (cast film) was immediately immersed into the 500-g precipitation bath containing the heparin (see Table 1) by carefully sliding the glass plate into the precipitation bath at as shallow an angle as possible.

The cast membranes were typically held in the precipitation bath for 1 hour. Shorter immersion times in the order of ca. 5 minutes did not result in any significant attachment of heparin. As shown in Example 6, the suitable immersion time varied depending on the initial heparin loading into the precipitation bath; the immersion time may vary from 10 to 60 min, or from 10 to 30 min, or from 30 to 60 min.

After 1-hour immersion, the glass plate and membrane were removed from the precipitation bath. The membrane was then washed under gently running deionized water for 1 minute. Then the membrane was immersed in 1 kg of a fresh water bath for 1 hour. After 1 hour, the membrane was washed with gently running deionized water for 1 minute, and was then allowed to air dry at ambient temperature.

Example 4

Comparison of Heparin Binding to Amine-Functionalized Copolymers (P1) by Ionic or Covalent Bond (Using the Toluidine Blue Staining Test)

Heparin immobilization was performed during the formation of a porous membrane via the in-situ "method (b)". Heparin sodium salt was contacted with an amine-functionalized PSU copolymer (P1-A), with or without coupling agent (containing EDC and NHS) in acidic water of pH 4.6 to form copolymer (P2-A) with ionically- or covalently-attached heparin while the membrane was being formed.

The amine-functionalized PSU copolymer (P1-A) originated from an allyl/vinylene-modified PSU copolymer (P0-A) formed with the three monomers: DCDPS, daBPA and BPA (as described in Example 1), in which the number of daBPA moles represented 9 mol % of the number of DCDPS moles while the number of BPA moles represented 91 mol % of the number of DCDPS moles.

Four membranes were formed via the in-situ method (b) by contacting the amine-functionalized PSU copolymer (P1-A) with 4 different loadings of heparin salt in the precipitation bath (without coupling agent) to achieve ionically-attached heparin PSU copolymer (P2-A).

Four other membranes were formed via the in-situ method (b) with 4 different loadings of heparin salt in the precipitation bath (with EDC and NHS as coupling agent) to achieve covalently-attached heparin PSU copolymer (P2-A).

Method for Measuring the Heparin Immobilization on Copolymer (P2) Staining of the Dried Membrane The glass plate with the membrane, or the membrane if detached, was immersed in approximately 100 g of toluidine blue solution for 1 minute. If the membrane was detached from the glass plate, one must carefully note concerning the membrane sides, which one was the glass side of the membrane and which one was the so-called air side of the membrane. If a shallow tray is used, the tray should be gently rocked to ensure movement of the toluidine solution over the membrane surface. The membrane was then washed under gently running deionized water for 1 minute, then air dried at ambient temperature.

A blue staining of the membrane is indicative of the presence of heparin. For PSU membranes which have been heparinized, thereby containing the heparin-functionalized copolymer (P2), that were detached from the glass plate, it was observed that only the air side of the membrane was stained, i.e., no heparin was attached to the glass side of the membrane.

Measurement of Heparin Attachment on Dried Membranes

A technique to assess the level of heparin on membrane surface measures the content in heparin present on a membrane surface, by measuring the toluidine blue uptake (staining) of a solid sample, such as a flat sheet membrane.

A digital image of the membrane surface can be made, and the image can be cropped to isolate a representative area of the stained membrane. The image is then analyzed by color separation. Color separation is a process of separating colors in the image. This process can be done through the k-means clustering algorithm. K-means clustering aims to partition 'n' data points into 'k' clusters (disjoint subsets) in which each data point belongs to the cluster with the nearest mean, serving as a prototype of the cluster. The 'k' just refers to the number of clusters desired in the final output. The 'data points' are colors, and the distance function is some measure of 'how different' two colors are. The k-means clustering algorithm lumps these colors into a given number of sets, and then calculate the mean color of each set. For example, a RGB image, sometimes referred to as a true color image, is stored as an m-by-n-by-3 data array that defines red, green, and blue color components for each individual pixel (data point). Online color separation tools can be found at http://mkweb.bcgsc.ca/colorsummarizer/ and https://www.dcode.fr/image-pixel-reader.

This color separation by k-means clustering algorithm generates tabulated data which provides, as average, a b* color value, useful for example to determine the blue stain related to heparin attachment. That is to say, for the analysis, the more heparin present, then the more toluidine blue has complexed resulting in a more blue-colored stain. Although this technique may not provide a quantitative assessment of the actual heparin loading on the membrane, it allows a relative comparison of various loadings of heparin in forming different PSU membranes which have been heparinized.

Results

Figure 2A:
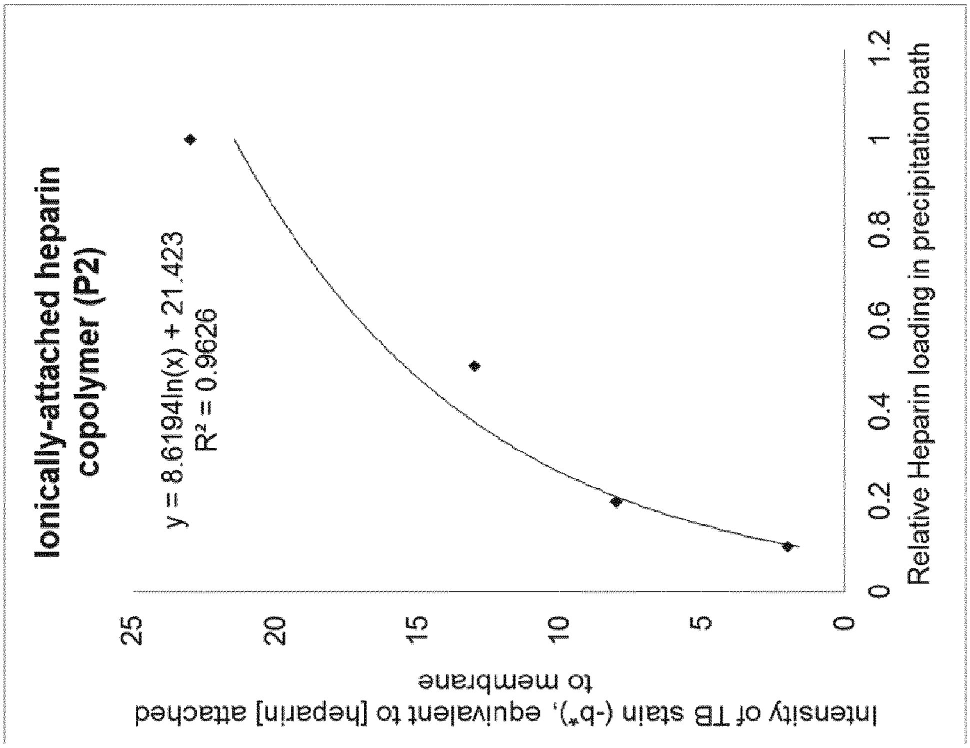
FIG. 2*a* shows the intensity of toluidine blue staining (b* value) with respect to relative amounts of heparin loadings in a precipitation bath used for forming PSU membranes containing ionically-attached heparin PSU copolymer (P2) according to one embodiment.
Figure 2B:
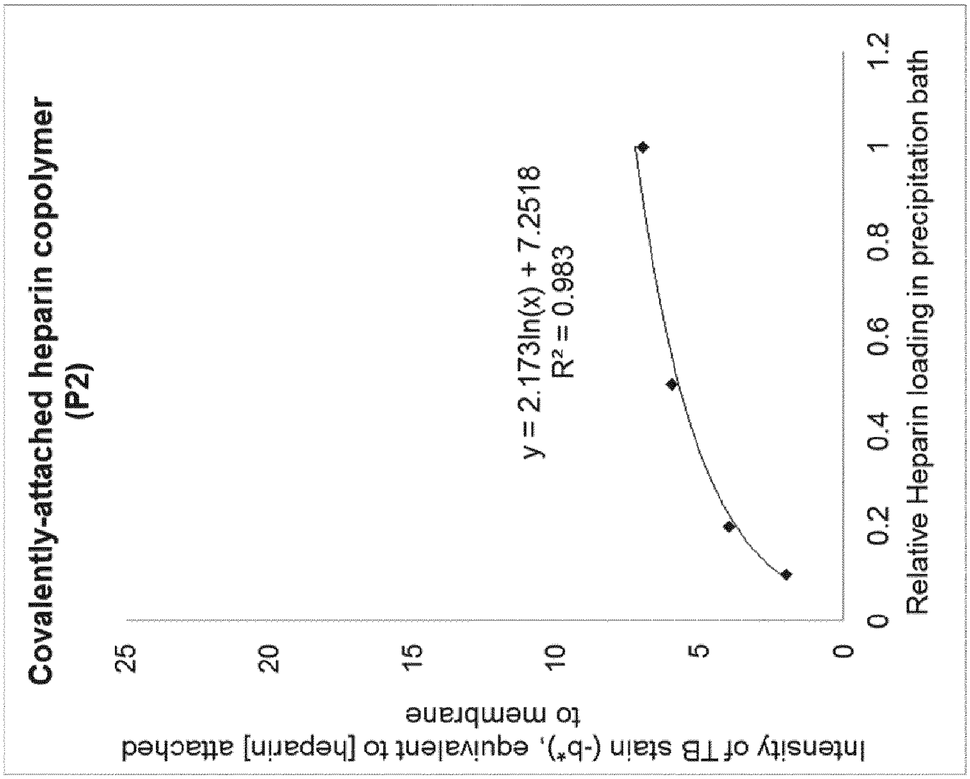
FIG. 2*b* shows the intensity of toluidine blue staining (b* value) with respect to relative amounts of heparin loadings in a precipitation bath used for forming PSU membranes containing covalently-attached heparin PSU copolymer (P2) according to one embodiment.

The intensity of the toluidine blue stain (−b* value) is reported for each of the formed membranes with respect to relative amounts of heparin loadings (e.g., 1, 0.5, 0.2 and 0.1) in the precipitation bath, in FIG. 2*a* for the membranes with the ionically-attached heparin PSU copolymer (P2) and FIG. 2*b* for the membranes with the covalently-attached heparin PSU copolymer (P2). In this instance, the highest heparin loading of 1500 ppm is represented with the relative amount of 1 while the lowest heparin loading of 150 ppm is represented with the relative amount of 0.1. It should be noted that the relative amount of heparin attached (as measured by the b* value of the heparin-toluidine complex) was a function of the relative amount of heparin in the precipitation bath.

Based on the toluidine blue staining protocol, the ionic attachment of heparin on the amine-functionalized PSU copolymer (P1) resulted in more efficient use of the heparin in the precipitation bath compared to its covalent attachment.

Also for a given and same amount of content of amine side chains in the amine-functionalized PSU copolymer (P1), higher levels of heparin attachment were achieved via ionic binding compared to covalent binding.

Example 5

Effect of Immersion Time with Heparin in Precipitation Bath During the in-Situ Method (b)

Various membranes were formed while carrying out the heparin immobilization using two different initial heparin contents (150 ppm, 1500 ppm) in the precipitation bath via the in-situ method (b).

The heparin sodium salt solution contacted the amine-functionalized PSU copolymer (P1), without coupling agent, in acidic water of pH 4.6 to form the copolymer (P2) with ionically-attached heparin, while the membrane was being formed.

The amine-functionalized PSU copolymer (P1) originated from an allyl/vinylene-modified PSU copolymer (P0) formed with the three monomers: DCDPS, daBPA and BPA (as described in Example 1), in which the number of daBPA moles represented 9 mol % of the number of DCDPS moles while the number of BPA moles represented 91 mol % of the number of DCDPS moles.

Figure 4:
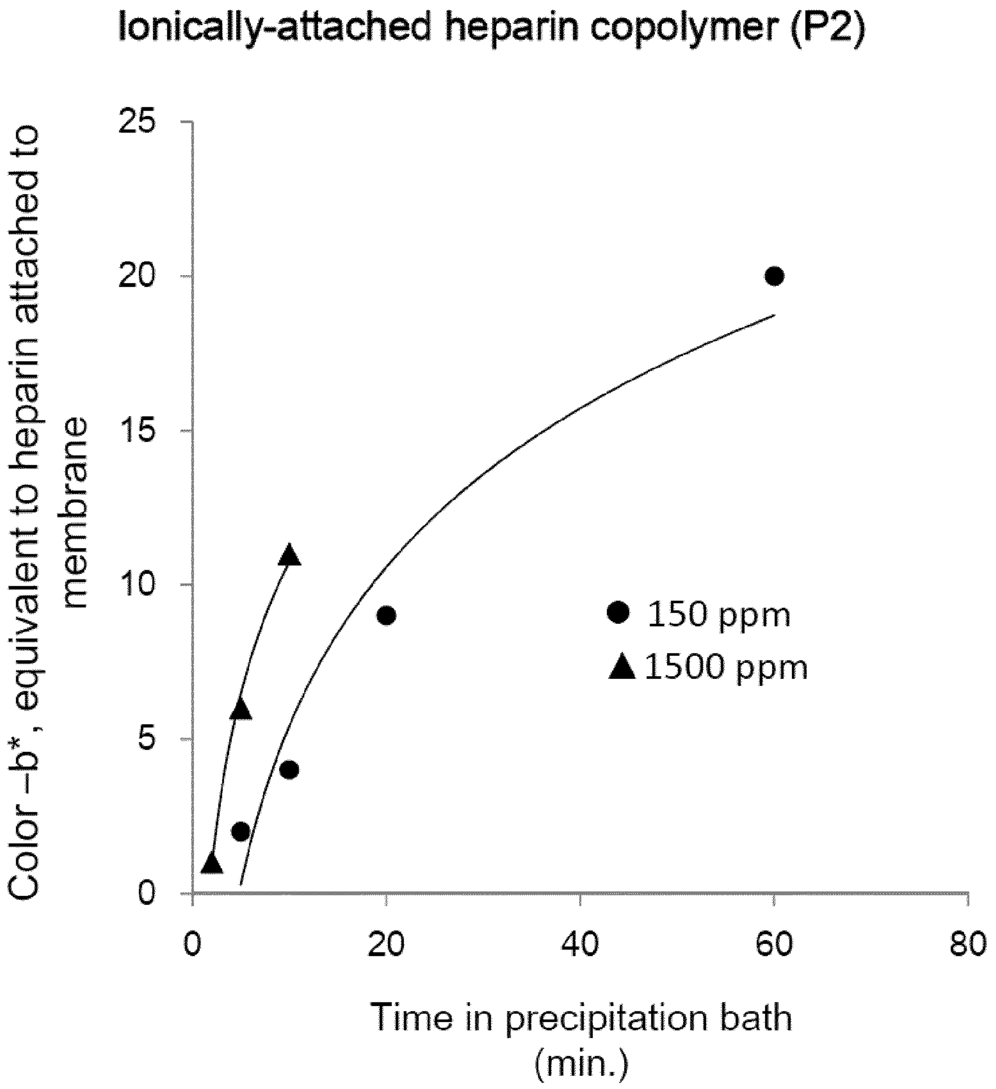
FIG. 4 compares the hemocompatibility (aPTT) test and the intensity of toluidine blue staining test for various PSU membranes modified with ionically-bound heparin according to one embodiment.

The intensity of the toluidine blue stain (b* value) of the membranes resulting from the ionically-attached heparin PSU copolymer (P2) is reported with respect to the time elapsed (up to 60 min) in the precipitation bath in FIG. 4.

It was observed that, for the higher initial heparin loading (1500 ppm) in the precipitation bath, the time for effective heparin attachment was quite rapid, in the order of 10 minutes.

On the other end, with the lower initial heparin loading (150 ppm) in the precipitation bath, the rate at which the heparin was attached appeared slower, steadily increasing with time and starting to level off around 30 minutes, and reaching a level of heparin attachment about two-fold higher than with higher heparin loading, as shown in the −b* color values in FIG. 4.

Example 6

Hemocompatibility (aPTT) of Heparin-Immobilized PSU Membranes

Hemocompatibility (aPTT) was measured for five heparin-immobilized PSU (P2) membranes (Samples 5-9) and three baseline PSU membranes (Samples 2-4). Baseline PSU membrane specimen were made with typical PSU (Sample 2), allyl-modified PSU=copolymer P0-A (Sample 3), and amine-functionalized PSU=copolymer P1-A (Sample 4). All membrane samples were made using a precipitation bath containing 5% DMAc in water. Samples 5-8 were made via the so-called in-situ process ("method (b)"), and Sample 9 was made via the so-called ex-situ process ("method (c)"). Heparin was ionically bound in the heparin-immobilized PSU Samples 5-7 & 9, while heparin was covalently bound using the coupling agent (EDS+NHS) in the heparin-immobilized PSU Sample 8. The heparin-containing bath used for immobilization had different initial heparin loadings: 1500 ppm for Samples 5, 8 & 9, 500 ppm for Sample 6 and 150 ppm for Sample 7.

Blood Coagulation Tests (Determination of the Activated Partial Thromboplastin Time "aPTT")

Hemocompatibility (aPTT) measures a coagulation (clotting) time of blood plasma. Typically, the difference in % of aPTT before and after the contact with the membrane specimen is quoted. The control sample was blood which was not in contact with the specimen. The activated partial thromboplastin time (aPTT) test was performed after the contact with porous flat sheet membranes.

The test procedure was the following:

- human fresh whole blood was put in a vial (a vial for each membrane sample) with sodium citrate;
- the contact was performed by immersing the membranes in the vials with whole blood in order to reach a surface/volume ratio of 6 $cm^2$/ml and incubated for 30 minutes at a temperature of 37° C.±1° C. in dynamic condition (orbital stirrer);
- this blood was then centrifuged at 3000 G for 20 minutes to obtain a supernatant plasma;
- aPTT was measured on this supernatant plasma.

Test plasma was finally mixed with a colloidal activator (magnesium aluminum silicate) followed by the addition of calcium chloride (solution with concentration of 0.025 mol/l) and clotting time was measured.

Results

The coagulation times expressed in seconds for the hemocompatibility (aPTT) test are reported in Table 2 for the control Sample 1, the five heparin-immobilized PSU membranes (Samples 5-9) and three baseline PSU membranes (Samples 2-4). The intensity of toluidine blue stain values are also reported in Table 2 for the five heparin-immobilized PSU membranes (Samples 5-9). The control sample refers to the clotting time measured on plasma coming from the blood which was not in contact with any membrane.

TABLE 2

| Description | Samples | Binding type for Heparin | Membrane Forming Method | aPTT Clotting time (s) | Intensity TB stain (−b* value) |
|---|---|---|---|---|---|
| Control sample | 1 | — | — | 28 | — |
| Baseline PSU membrane | 2 | — | — | 26.9 | — |
| Baseline PSU Copolymer (P0-A) membrane | 3 | — | — | 26.7 | — |
| Baseline PSU Copolymer (P1-A) membrane | 4 | — | — | 26.7 | — |
| Heparin-modified PSU membrane | 5 | Ionic binding | in-situ method (b) | 116 | 23 |
| Heparin-modified PSU membrane | 6 | Ionic binding | in-situ method (b) | 63.3 | 13 |
| Heparin-modified PSU membrane | 7 | Ionic binding | in-situ method (b) | 40.6 | 8 |
| Heparin-modified PSU membrane | 8 | Covalent(1) binding | in-situ method (b) | 41.1 | 7 |
| Heparin-modified PSU membrane | 9 | Ionic binding | ex-situ method (c) | 175.3 | 8 |

(1)with coupling agent

It was observed that there was a very large difference in hemocompatibility (aPTT) between the heparin-immobilized PSU membranes (Samples 5-9) and the control PSU membranes (Samples 2-4). In other words, plasma extracted from the blood in contact with the membranes modified with heparin (Samples 5-9) coagulated much slower compared to blood plasma in contact with the baseline PSU membranes (Samples 2-4). Also, only heparin-immobilized membranes (Samples 5-9) showed a significant increase of coagulation times compared to the Control Sample 1 in which the blood plasma did not come in contact with any membrane.

Example 7

Figure 3:
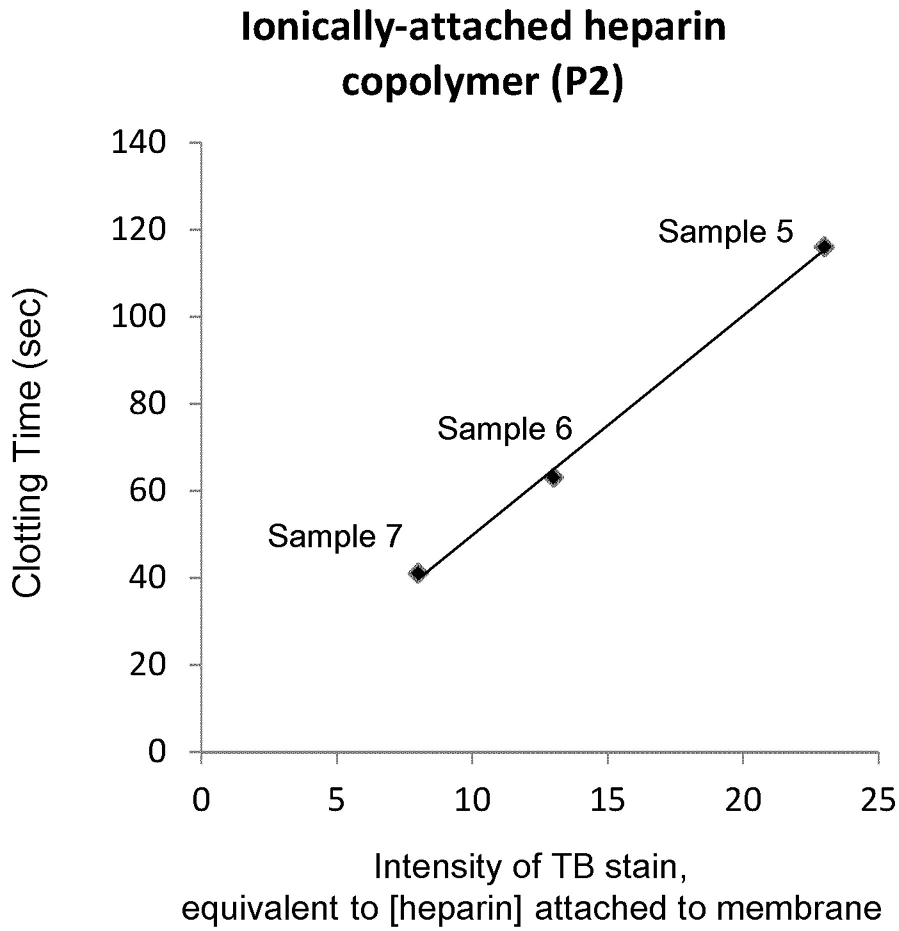
FIG. 3 illustrates the intensity of toluidine blue staining (b* value) with respect to the time elapsed in the precipitation bath used for forming PSU membranes containing ionically-attached heparin PSU copolymer (P2) according to one embodiment.

Comparison of Hemocompatibility (aPTT) Versus Intensity of Toluidine Blue Stain for Heparin-Immobilized PSU (P2) Membranes The hemocompatibility (aPTT) test and the intensity of toluidine blue stain test were compared for the PSU membranes modified with ionically-bound heparin (Samples 5-7) in FIG. 3.

As shown in FIG. 3, Samples 5-7 contained decreasing levels of immobilized heparin, as determined by staining with toluidine blue. In correspondence with the toluidine blue stain test, the blood clotting time (via aPTT) was increased as the level of immobilized heparin increased.

Example 8

Comparison of Heparin Binding to Amine-Functionalized Copolymers (P1) by In-Situ Method (b) or Ex-Situ Method (c)

Heparin immobilization was performed during the formation of a porous membrane via the in-situ method (b), that is to say, heparin sodium salt was contacted with an amine-functionalized PSU copolymer (P1) to form the copolymer (P2) with ionically or covalently attached heparin at the same time as the membrane was formed.

For comparison, immobilization of heparin was carried out to a pre-formed amine-functionalized PSU porous membrane (immediately after being washed) via the ex-situ method (c). Several pre-formed porous membranes were contacted with various contents of heparin sodium salt and allowed to soak in a water bath for 1 hour to form the copolymer (P2) with ionically or covalently attached heparin. The soaked porous membranes were washed and then air dried.

Figure 5:
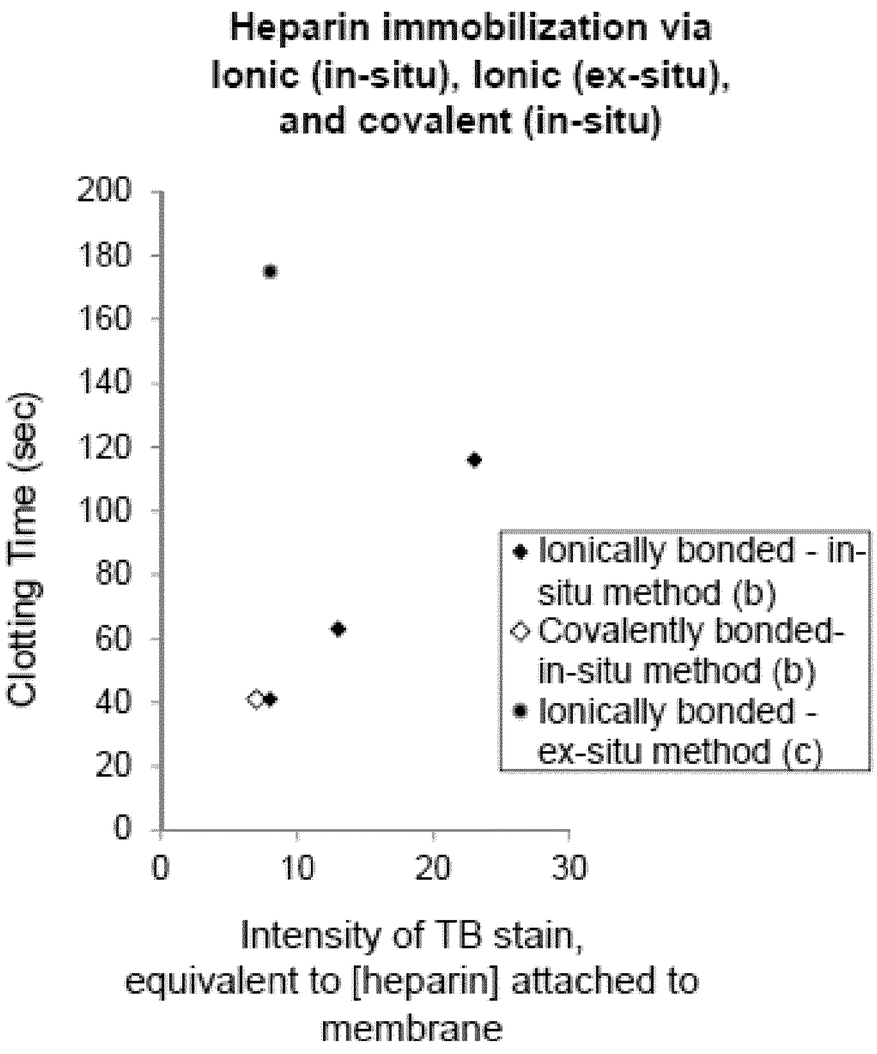
FIG. 5 compares the hemocompatibility (aPTT) test and the intensity of toluidine blue staining test for various heparin-modified PSU membranes with in-situ heparin ionic binding, ex-situ heparin ionic binding and in-situ heparin covalent binding according to several embodiments.

The hemocompatibility (aPTT) test and the intensity of toluidine blue stain test were compared in FIG. 5 for in-situ heparin ionic binding, ex-situ heparin ionic binding and in-situ heparin covalent binding.

The hemocompatibility testing indicated that for the same heparin loading determined by same –b* color value in toluidine blue staining test, the efficacy/activity for aPTT of the attached heparin was higher when the heparin was immobilized by the ex-situ method (c) on a preformed membrane containing the amine-functionalized copolymer (P1). Although not willing to be limited by any theory, it is believed that the manner with which the heparin may be attached in the copolymer (P2) affects the conformation of the heparin on the surface of the membrane, and therefore also impacts the availability of the heparin regions which interact with the various blood components that cause a cascade of chemical processes which eventually leads to blood clotting.

It was also shown that for in-situ method (b), the level of heparin attachment was much improved with ionic binding compared to covalent binding.

While preferred embodiments of this invention have been shown and described, modifications thereof can be made by one skilled in the art without departing from the spirit or teaching of this invention. The embodiments described herein are exemplary only and are not limiting. Many variations and modifications of systems and methods are possible and are within the scope of the invention. Accordingly, the scope of protection is not limited by the description set out above, but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention.

The invention claimed is:

1. A copolymer (P2) comprising:

recurring units ($R_{P2}$) of formula (M):

(M)

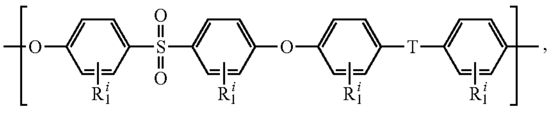

recurring units ($R^*_{P2}$) of formula (Q):

(G)

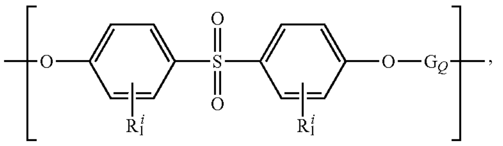

wherein each $R_1$ is independently selected from the group consisting of a halogen, alkyl, alkenyl, alkynyl, aryl, ether, thioether, carboxylic acid, ester, amide, imide, alkali metal sulfonate, alkaline earth metal sulfonate, alkyl sulfonate, alkali metal phosphonate, alkaline earth metal phosphonate, alkyl phosphonate, amine and quaternary ammonium;

each i is an integer independently selected from 0 to 4;

T is selected from the group consisting of a bond, $—CH_2—$; $—O—$; $—SO_2—$; $—S—$; $—C(O)—$; $—C(CH_3)_2—$; $—C(CF_3)_2—$; $—C(=CCl_2)—$; $—C(CH_3)(CH_2CH_2COOH)—$; $—N=N—$; $—R_aC=CR_b—$, where each $R_a$ and $R_b$, independently of one another, is a hydrogen or a C1-C12-alkyl, C1-C12-alkoxy, or C6-C18-aryl group; $—(CF_2)_m—$ with m being an integer from 1 to 6; an aliphatic divalent group, linear or branched, of up to 6 carbon atoms; and combinations thereof;

$G_Q$ is selected from the group consisting of at least one of the following formulae ($G_{Q1}$), ($G_{Q2}$), ($G_{Q3}$), ($G_{Q4}$), ($G_{Q5}$), or ($G_{Q6}$):

($G_{Q1}$)

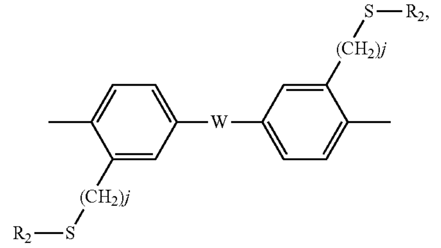

-continued ($G_{Q2}$)

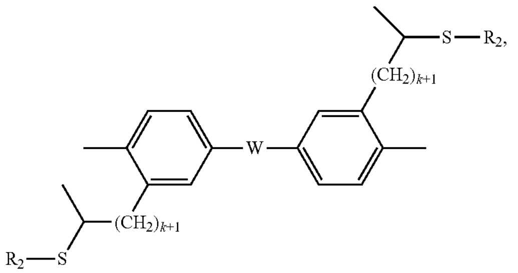

($G_{Q3}$)

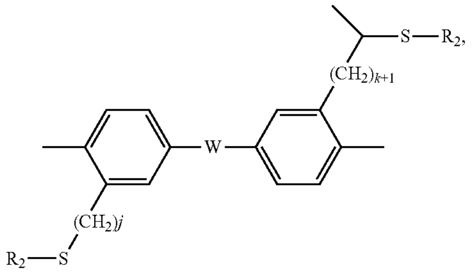

($G_{Q4}$)

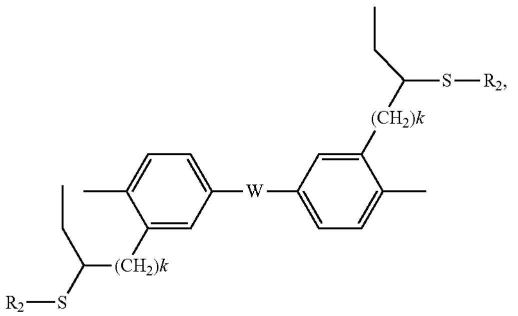

($G_{Q5}$)

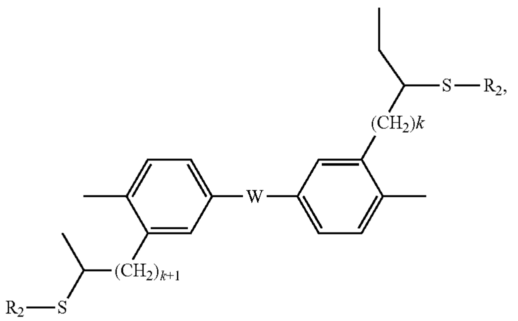

-continued ($G_{Q6}$)

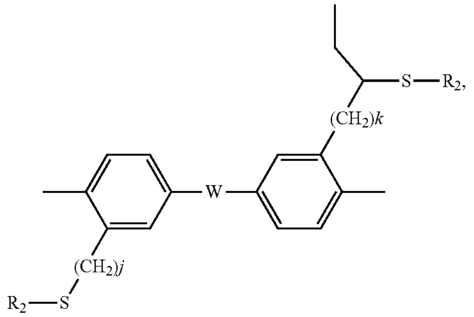

wherein each k is an integer independently selected from 0 to 4;

each j is an integer independently selected from 2 to 7;

W is a bond, $—C(CH_3)_2—$ or $—SO_2—$;

$R_2$ is represented by the following formula: $—(CH_2)_p—NR_cB$, with p being an integer selected from 1 to 5, with Rc being independently a C1-C6 alkyl or H, and with B representing a bioactive compound which is covalently and/or ionically bound to $R_2$; and B being selected from the group consisting of:

antithrombotic agents or derivatives thereof, amino acids, nucleic acids, glucuronic acid residues, hyaluronic acid or derivatives thereof, proteins, metal-chelating and/or protease inhibitor agents;

acidic lipids, and any combinations of two or more compounds thereof.

2. The copolymer (P2) of claim 1, wherein T in the recurring units ($R_{P2}$) is selected from the group consisting of a bond, $—SO_2—$ and $—C(CH_3)_2—$.

3. The copolymer (P2) of claim 1, wherein i is zero for each $R_1$ of the recurring units ($R_{P2}$) and the recurring units ($R^*_{P2}$).

4. The copolymer (P2) of claim 1, wherein k is 0 and j is 3 in the recurring units ($R^*_{P2}$).

5. The copolymer (P2) of claim 1, wherein the molar ratio of the recurring units ($R_{P2}$)/recurring units ($R^*_{P2}$) varies between 0.01/100 to 100/0.01.

6. The copolymer (P2) of claim 1, wherein the recurring units ($R_{P2}$) have a formula according to formulae (M1), (M2) or (M3):

(M1)

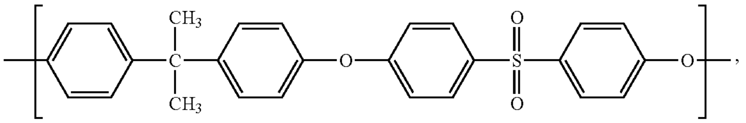

(M2)

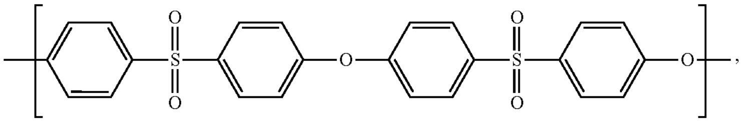

-continued (M3)

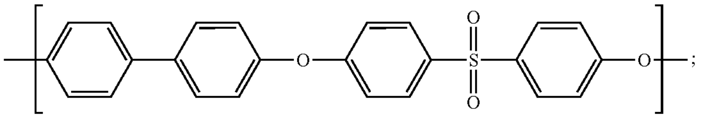

7. The copolymer (P2) of claim 1, wherein $R_2$ in at least one of the formulae ($G_{Q1}$), ($G_{Q2}$), ($G_{Q3}$), ($G_{Q4}$), ($G_{Q5}$), ($G_{Q6}$) is: —$(CH_2)_2$—NHB.

8. The copolymer (P2) of claim 1, comprising collectively at least 50 mol. % of the recurring units ($R_{P2}$) and ($R^*_{P2}$), based on the total number of moles of recurring units in the copolymer (P2).

9. The copolymer (P2) of claim 1, further comprising recurring units ($R^*_{P1}$) of formula (N):

(N)

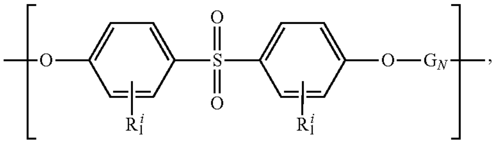

wherein each $R_1$ and each i are the same as in the recurring units ($R^*_{P2}$);

$G_N$ is at least one formula selected from the group consisting of following formulae ($G_{N1}$), ($G_{N2}$), ($G_{N3}$), ($G_{N4}$), ($G_{N5}$) and ($G_{N6}$):

($G_{N1}$)

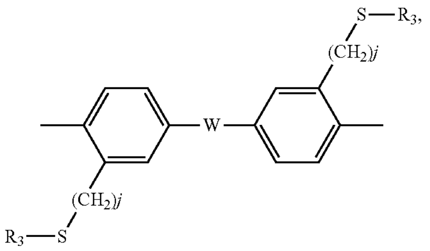

($G_{N2}$)

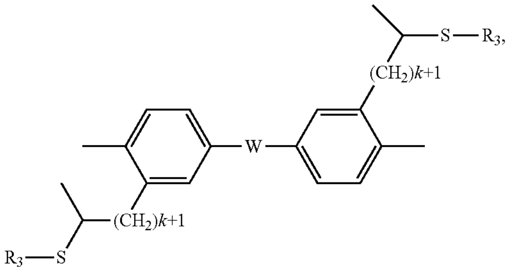

-continued ($G_{N3}$)

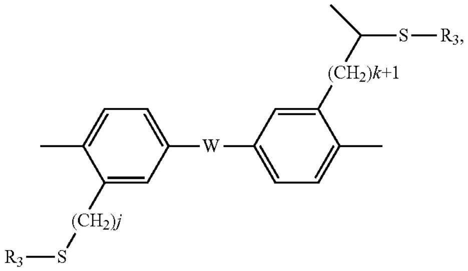

($G_{N4}$)

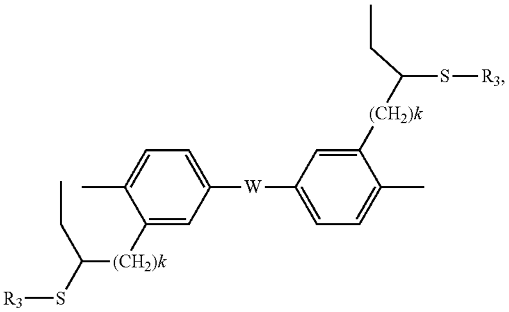

($G_{N5}$)

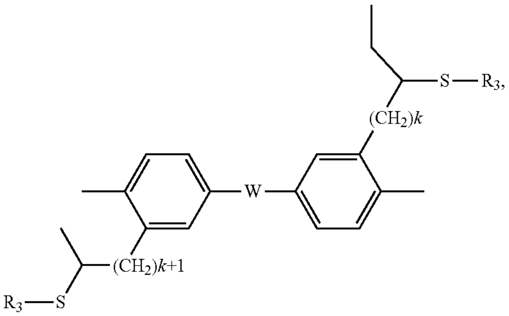

($G_{N6}$)

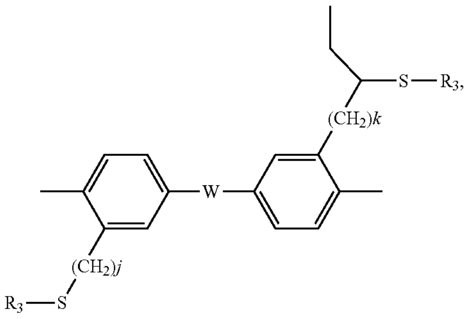

wherein each k is an integer independently selected from 0 to 4;

each j is an integer independently selected from 2 to 7;

W is a bond, —$C(CH_3)_2$— or —$SO_2$—, preferably —$C(CH_3)_2$— or —$SO_2$—, more preferably € $(CH_3)_2$ —;

$R_3$ is represented by the following formula: —$(CH_2)_p$—$NHR_c$, with p being selected from 1 to 5, with Rc being independently a C1-C6 alkyl or H.

10. The copolymer (P2) of claim 1, wherein B in $R_2$ is a bioactive compound selected from the group consisting of antithrombotic agents or derivatives thereof.

11. A process for preparing the copolymer (P2) of claim 1, comprising:

contacting a copolymer (P1) with a bioactive compound or derivative thereof, optionally in the presence of a coupling agent, in an acidic aqueous solvent, to bind the bioactive compound to the copolymer (P1) to make the copolymer (P2), said polymer (P1) comprising:

recurring units ($R_{P1}$) of said formula (M) which is same as the recurring units ($R_{P2}$), and recurring units ($R^*_{P1}$) of formula (N):

(N)

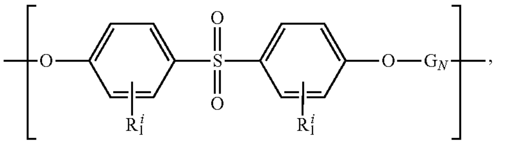

wherein each $R_1$ and each i are the same as in the recurring units ($R^*_{P2}$); and $G_N$ is at least one formula selected from the group consisting of following formulae ($G_{N1}$), ($G_{N2}$), ($G_{N3}$), ($G_{N4}$), ($G_{N5}$) and ($G_{N6}$):

($G_{N1}$)

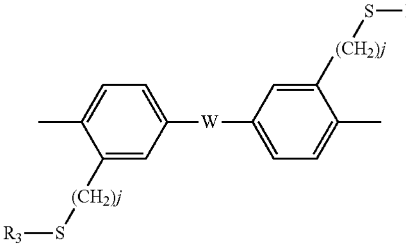

($G_{N2}$)

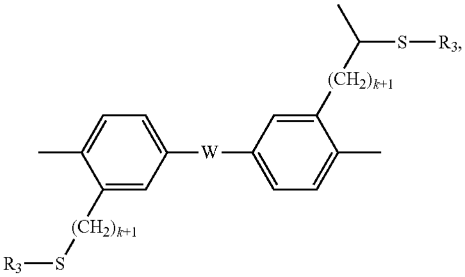

-continued ($G_{N3}$)

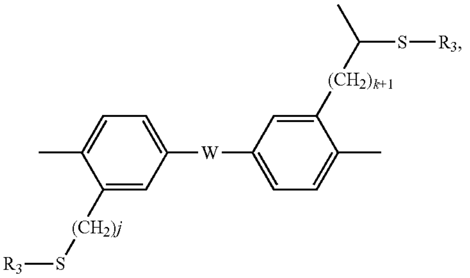

($G_{N4}$)

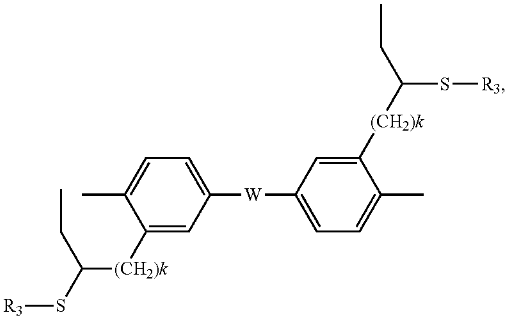

($G_{N5}$)

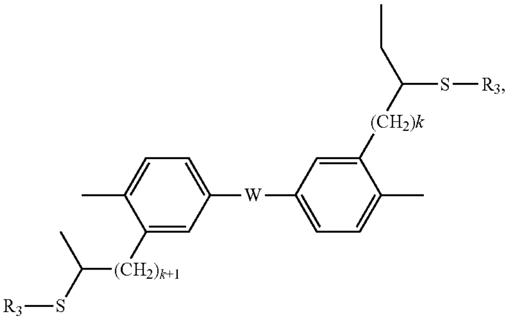

($G_{N6}$)

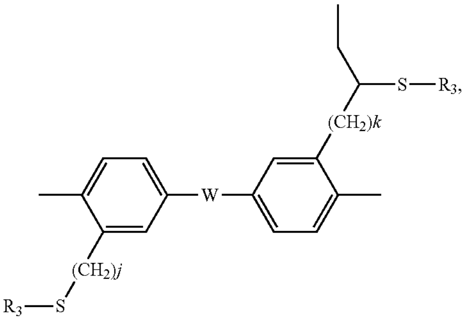

wherein each k is an integer independently selected from 0 to 4;

each j is an integer independently selected from 2 to 7;

W is a bond, —$C(CH_3)_2$— or —$SO_2$—; and $R_3$ is represented by the following formula: —$(CH_2)_p$—$NHR_c$, with p being selected from 1 to 5, with $R_c$ being independently a C1-C6 alkyl or H.

12. The process of claim 11, wherein the coupling agent is used in the process to covalently bind the bioactive compound to the copolymer (P1), and wherein the coupling agent comprises at least one compound selected from the group consisting of N-(3-Dimethylaminopropyl)-N'-ethylcarbodiimide hydrochloride (EDC), N-Hydroxy succinimide (NHS), 1-[3-(Dimethylamino)propyl]-3-ethylcarbodiimide methiodide, 1-(3-Dimethylaminopropyl)-3-ethylcarbodiimide, which is polymer-bound, HOAt (1-Hydroxy-7-azabenzotriazole), PyBOP (benzotriazol-1-yl-oxytripyrrolidinophosphonium hexafluorophosphate), and PyAOP ((7-Azabenzotriazol-1-yloxy)tripyrrolidinophosphonium hexafluorophosphate).

13. A method for preparing an article or a part thereof, comprising using the copolymer (P2) of claim 1 in forming the article or part thereof, said article being selected from the group consisting of medical devices, implants, membranes, coatings, melt processed films, solution processed films, melt process monofilaments and fibers, solution processed monofilaments, hollow fibers and solid fibers, coatings, printed objects, and injection and compression molded objects.

14. A method for preparing an article comprising the copolymer (P2) of claim 1, comprising:

performing one of the following methods:

method a): using the copolymer (P2) in forming the article or part thereof, preferably via phase inversion occurring in a liquid phase; or method b): contacting a copolymer (P1) with a bioactive compound or derivative thereof to make the copolymer (P2) while at the same time forming the article or part thereof; or method c): contacting a pre-formed article or part thereof comprising a copolymer (P1) with a bioactive compound or derivative thereof to make the copolymer (P2);

wherein the contacting step in said method (b) or (c) is carried out, optionally in the presence of a coupling agent, in an acidic aqueous solvent, preferably of pH from 3 the 6, or from 4.2 to 5, of from 4.4 to 4.8, to bind the bioactive compound to the copolymer (P1) to make the copolymer (P2), and wherein the copolymer (P1) comprises:

recurring units ($R_{P1}$) of said formula (M), and recurring units ($R^*_{P1}$) of formula (N):

(N)

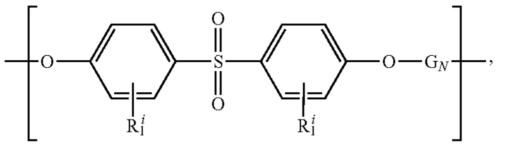

wherein

T is the same as in the recurring units ($R_{P2}$);

each $R_1$ and each i are the same as in the recurring units ($R^*_{P2}$); and $G_N$ is at least one formula selected from the group consisting of following formulae ($G_{N1}$), ($G_{N2}$), ($G_{N3}$), ($G_{N4}$), ($G_{N5}$) and ($G_{N6}$):

($G_{N1}$)

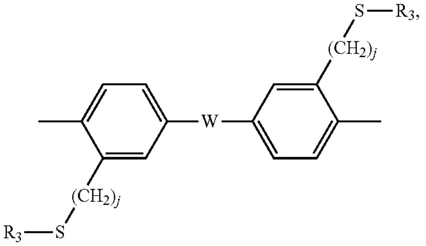

-continued ($G_{N2}$)

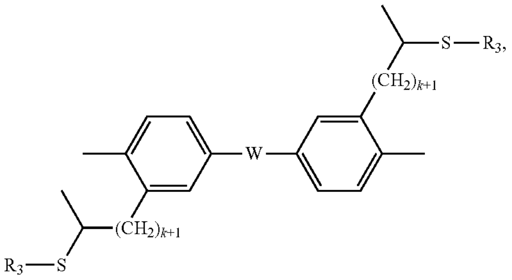

($G_{N3}$)

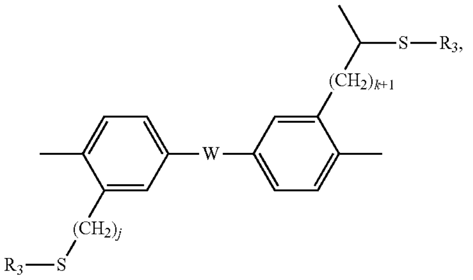

($G_{N4}$)

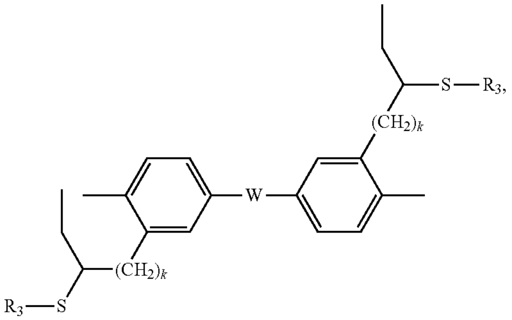

($G_{N5}$)

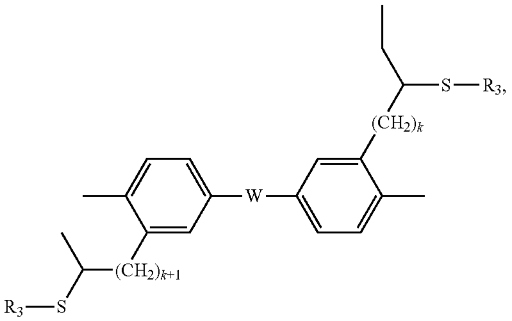

($G_{N6}$)

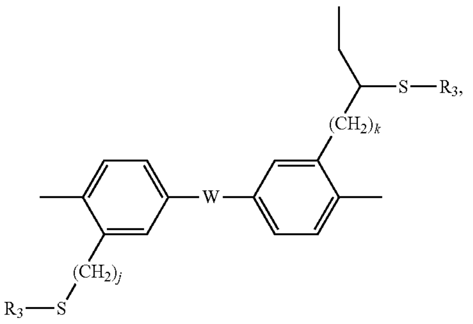

wherein each k is an integer independently selected from 0 to 4;

each j is an integer independently selected from 2 to 7;

W is a bond, —$C(CH_3)_2$— or —$SO_2$—;

$R_3$ is represented by the following formula: —$(CH_2)_p$—$NHR_c$, with p being selected from 1 to 5, with $R_c$ being independently a C1-C6 alkyl or H.

15. An article comprising the copolymer (P2) of claim 1, being selected from the group consisting of medical devices, implants, membranes, coatings, melt processed films, solution processed films, melt process monofilaments and fibers, solution processed monofilaments, hollow fibers and solid fibers, coatings, printed objects, and injection and compression molded objects.

16. The copolymer (P2) of claim 1, wherein the molar ratio of the recurring units ($R_{P2}$)/recurring units ($R^*_{P2}$) varies from 1/1 to 20/1.

17. The copolymer (P2) of claim 1, wherein the bioactive compound is heparin or salts thereof.

18. The method of claim 14, wherein, when the article is a membrane or a part thereof, the method includes a phase inversion occurring in a liquid phase to form the membrane or part thereof.

* * * * *